United States Patent
Mohapatra et al.

(10) Patent No.: US 11,016,062 B2
(45) Date of Patent: May 25, 2021

(54) SYSTEM AND METHOD OF MEASURING CELL VIABILITY AND GROWTH

(71) Applicants: Shyam S. Mohapatra, Lutz, FL (US); Subhra Mohapatra, Lutz, FL (US); Rasim Oytun Guldiken, Tampa, FL (US); Rajesh R. Nair, Tampa, FL (US); Tao Wang, Tampa, FL (US)

(72) Inventors: Shyam S. Mohapatra, Lutz, FL (US); Subhra Mohapatra, Lutz, FL (US); Rasim Oytun Guldiken, Tampa, FL (US); Rajesh R. Nair, Tampa, FL (US); Tao Wang, Tampa, FL (US)

(73) Assignees: University of South Florida, Tampa, FL (US); TransGenex Nanobiotech, Inc., Lutz, FL (US)

( * ) Notice: Subject to any disclaimer, the term of this patent is extended or adjusted under 35 U.S.C. 154(b) by 0 days.

(21) Appl. No.: 16/722,210

(22) Filed: Dec. 20, 2019

(65) Prior Publication Data
US 2020/0141905 A1 May 7, 2020

Related U.S. Application Data

(60) Division of application No. 15/682,070, filed on Aug. 21, 2017, now Pat. No. 10,520,472, which is a
(Continued)

(51) Int. Cl.
*G01N 29/02* (2006.01)
*G01N 29/036* (2006.01)
(Continued)

(52) U.S. Cl.
CPC ......... *G01N 29/022* (2013.01); *G01N 29/036* (2013.01); *G01N 29/222* (2013.01);
(Continued)

(58) Field of Classification Search
CPC .. G01N 29/022; G01N 29/036; G01N 29/222; G01N 29/2462; G01N 2291/02466; G01N 2291/02475; G01N 33/48
(Continued)

(56) References Cited

U.S. PATENT DOCUMENTS

| 7,878,063 B1 | 2/2011 | Cular et al. |
| 7,964,144 B1 | 6/2011 | Nordin et al. |

(Continued)

FOREIGN PATENT DOCUMENTS

| CN | 104328040 B | 4/2016 |
| EP | 2017612 A1 | 1/2009 |
| WO | 2013074125 A1 | 5/2013 |

OTHER PUBLICATIONS

Wang et al. Sensors, vol. 15, Dec. 19, 2015, p. 32045-32055.*
(Continued)

*Primary Examiner* — Maureen Wallenhorst
(74) *Attorney, Agent, or Firm* — Michele L. Lawson; Smith & Hopen, P.A.

(57) ABSTRACT

A novel SH-SAW biosensor capable of non-invasive and touch-free detection of cancer cell viability and growth or proliferation in two-dimensional (2D) and three-dimensional (3D) cell cultures as well as stem cell regeneration as it pertains to cancer cell biology and anti-cancer drug development is presented. The biosensor includes two pairs of resonators including interdigital transducers reflecting fingers to quantify mass loading by the cells in suspension as well as within a tumoroid culture platform. The biosensor can be part of a perfused 3PNS-tumoroid system that is amenable to real-time non-invasive monitoring of the cell proliferation, viability, and multiplexed detection of key physiologic and clinical biomarkers.

14 Claims, 20 Drawing Sheets

Related U.S. Application Data continuation of application No. PCT/US2016/018762, filed on Feb. 19, 2016.

(60) Provisional application No. 62/118,300, filed on Feb. 19, 2015, provisional application No. 62/252,051, filed on Nov. 6, 2015.

(51) Int. Cl.
  *G01N 29/22* (2006.01)
  *G01N 29/24* (2006.01)
  *G01N 33/48* (2006.01)

(52) U.S. Cl.
  CPC ......... *G01N 29/2462* (2013.01); *G01N 33/48* (2013.01); *G01N 2291/02466* (2013.01); *G01N 2291/02475* (2013.01)

(58) Field of Classification Search
  USPC .............. 436/63, 81; 435/29, 325, 366, 7.23; 310/313 A, 313 B, 313 R
  See application file for complete search history.

(56) References Cited

U.S. PATENT DOCUMENTS

| | | | |
|---|---|---|---|
| 8,669,688 | B1 | 3/2014 | Branch |
| 8,709,791 | B2 | 4/2014 | Larson et al. |
| 10,520,472 | B2* | 12/2019 | Mohapatra ........... G01N 29/036 |
| 2010/0088039 | A1 | 4/2010 | Yang et al. |
| 2013/0009517 | A1 | 1/2013 | Do et al. |
| 2013/0224860 | A1 | 4/2013 | Mohapatra et al. |
| 2015/0024967 | A1 | 1/2015 | Mohapatra et al. |
| 2017/0052174 | A1 | 2/2017 | Branch et al. |

OTHER PUBLICATIONS

Girard, Yvonne K. et al. A 3D Fibrous Scaffold Inducing Tumoroids: A Platform for Anticancer Drug Development. PLOS One, Oct. 2013. vol. 8, Issue 10, e75345.
Shen, Chi-Yen and Shih-Yuan Liou. Surface acoustic wave monitor for ppm ammonia detection. Sensors and Actuators B 131 (2008) 673-679.
Onen, Onursal, et al. A Urinary Bcl-2 Surface Acoustic Wave Biosensor for Early Ovarian Cancer Detection. Sensors 2012, 12, 7423-7437; doi: 10.3390/s120607423.
Vivancos, Jose-Luis, et al. Surface acoustic wave based analytical system for the detection of liquid detergents. Sensors and Actuators B 171-172 (2012) 469-477.
Pomowski, Anett, et al. Acoustice Biosensors Coated With Phosphorylcholine Groups for Label-Free Detection of Human C-Reactive Protein in Serum. IEEE Sensors Journal, vol. 15, No. 8, Aug. 2015. pp. 4388-4392.
Nomura, T., et al. Measurement of acoustic properties of liquid using liquid flow SH-SAW sensor system. Sensors and Actuators B 76 (2001), 69-73.
Deobagkar, Deepti D., et al. Acoustic wave immunosensing of *Escherichia coli* in water. Sensors and Actuators B 104 (2005) 85-89.
Roederer, Joy E. and Glenn J. Bastiaans. Microgravimetric Immunoassay with Piezoelectric Crystals. Anal. Chem. 1983, 2333-2336.
Kondoh, Jun, et al. Development of methanol sensor using a shear horizontal surface acoustic wave device for a direct methanol fuel cell. Sensors and Actuators B 129 (2008) 575-580.
Nomura, T., et al. Liquid sensor probe using reflecting SH-SAW delay line. Sensors and Actuators B 91 (2003) 298-302.
Jo, Myeong Chan and Rasim Guldiken. Effects of polydimethylsiloxane (PDMS) microchannels on surface acoustic wave-based microfluidic devices. Microelectronic Engineering 113 (2014) 98-104.
Oh, Haekwan, et al. Development of a high sensitive pH sensor based on shear horizontal surface acoustic wave with ZnO nanoparticles. Microelectronic Engineering 111 (2013) 154-159.
Chivukula, Venkata, et al. ZnO nanoparticle surface acoustic wave UV sensor. Applied Physics Letters 96, 233512(2010).
Powell, David A., et al. Numerical calculation of SAW sensitivity: application to ZnO/LiTaO3 transducers. Sensors and Actuators A 115 (2004) 456-461.
Powell, David A., et al. A Layered SAW Device Based on ZnO/LiTaO3 for Liquid Media Sensing Applications. 2002 IEEE Ultrasonics Symposium-493.
Chang, Ren-Chuan, et al. A study of Love wave devices in ZnO/Quartz and ZnO/LiTaO3 structures. Thin Solid Films 498 (2006) 146-151.
Fu, Y.Q., et al. Recent developments on ZnO films for acoustic wave based bio-sensing and microfluidic applications: a review. Sensors and Actuators B 143 (2010) 606-619.
Rocha-Gaso, Maria-Isabel, et al. Surface Generated Acoustic Wave Biosensors for the Detection of Pathogens: A Review. Sensors 2009, 9, 5740-5769; doi:10.3390/s90705740.
Guldiken, Rasim, et al. Sheathless Size-Based Acoustic Particle Separation. Sensors 2012, 12, 905-922; doi: 10.3390/s120100905.
Jo, Myeong Chan and Rasim Guldiken. Active density-based separation using standing surface acoustic waves. Sensors and Actuators A 187 (2012) 22-28.
Jo, Myeong Chan and Rasim Guldiken. Dual surface acoustic wave-based active mixing in a microfluidic channel. Sensors and Actuators A 196 (2013) 1-7.
Pang, Hua-Feng, et al. Love mode surface acoustic wave ultraviolet sensor using ZnO films deposited on 36 Y-cut LiTaO3. Sensors and Actuators A 193 (2013) 87-94.
Moya, Monica, et al. An integrated in vitro model of perfused tumor and cardiac tissue. Stem Cell Research & Therapy 2013, 4(Suppl 1):S15. http://stemcellres.com/content/4/S1/S15.
Walsh, Colin L., et al. A multipurpose microfluidic device designed to mimic microenvironment gradients and develop targeted cancer therapeutics. Lab Chip, 2009, 9, 545-554.
Hattersley, Samantha M., et al. A Microfluidic System for Testing the Responses of Head and Neck Squamous Cell Carcinoma Tissue Biopsies to Treatment with Chemotherapy Drugs. Annals of Biomedical Engineering, vol. 40, No. 6, Jun. 2012. pp. 1277-1288. DOI:10.1007/s10439-011-0428-9.
International Search Report and Written Opinion issued by the International Searching Authority dated May 6, 2016 for corresponding International Patent Application No. PCT/US2016/018762.
International Preliminary Report on Patentability issued by the International Bureau dated Aug. 31, 2017 for corresponding International Patent Application No. PCT/US2016/018762.
Restriction Requirement issued by the USPTO dated Apr. 8, 2019 for priority U.S. Appl. No. 15/682,070.
Non-Final Office Action issued by the USPTO dated Jul. 23, 2019 for priority U.S. Appl. No. 15/682,070.

\* cited by examiner

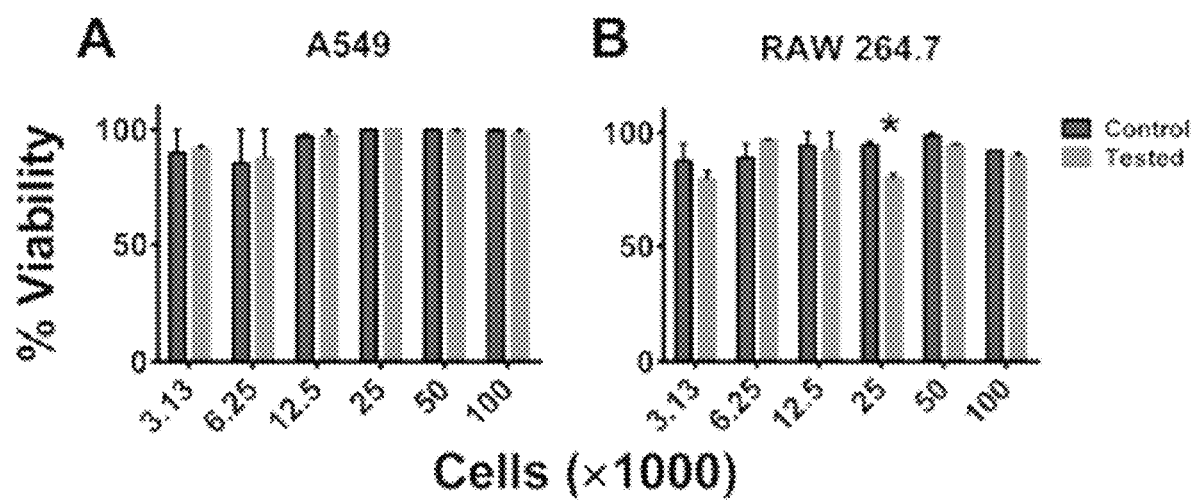
Figure 3A-B

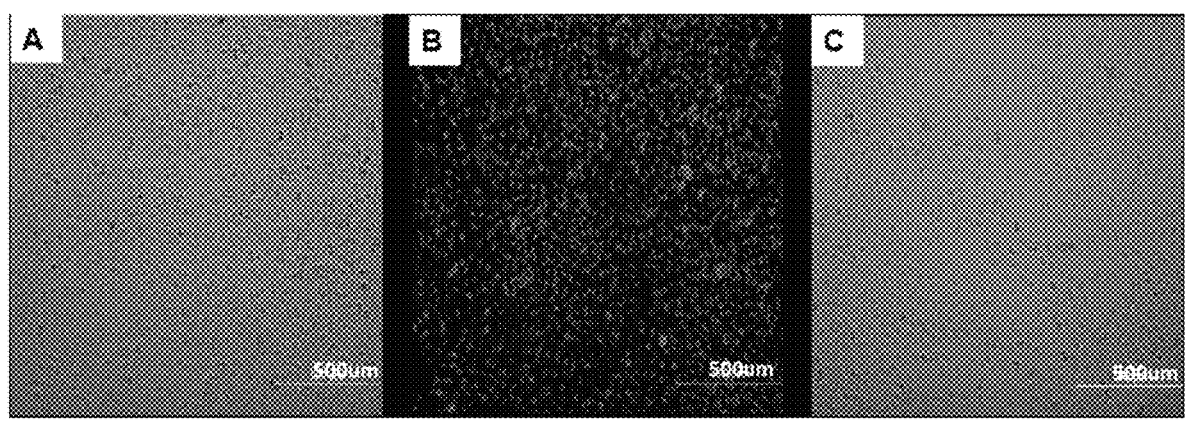
Figure 4A-C

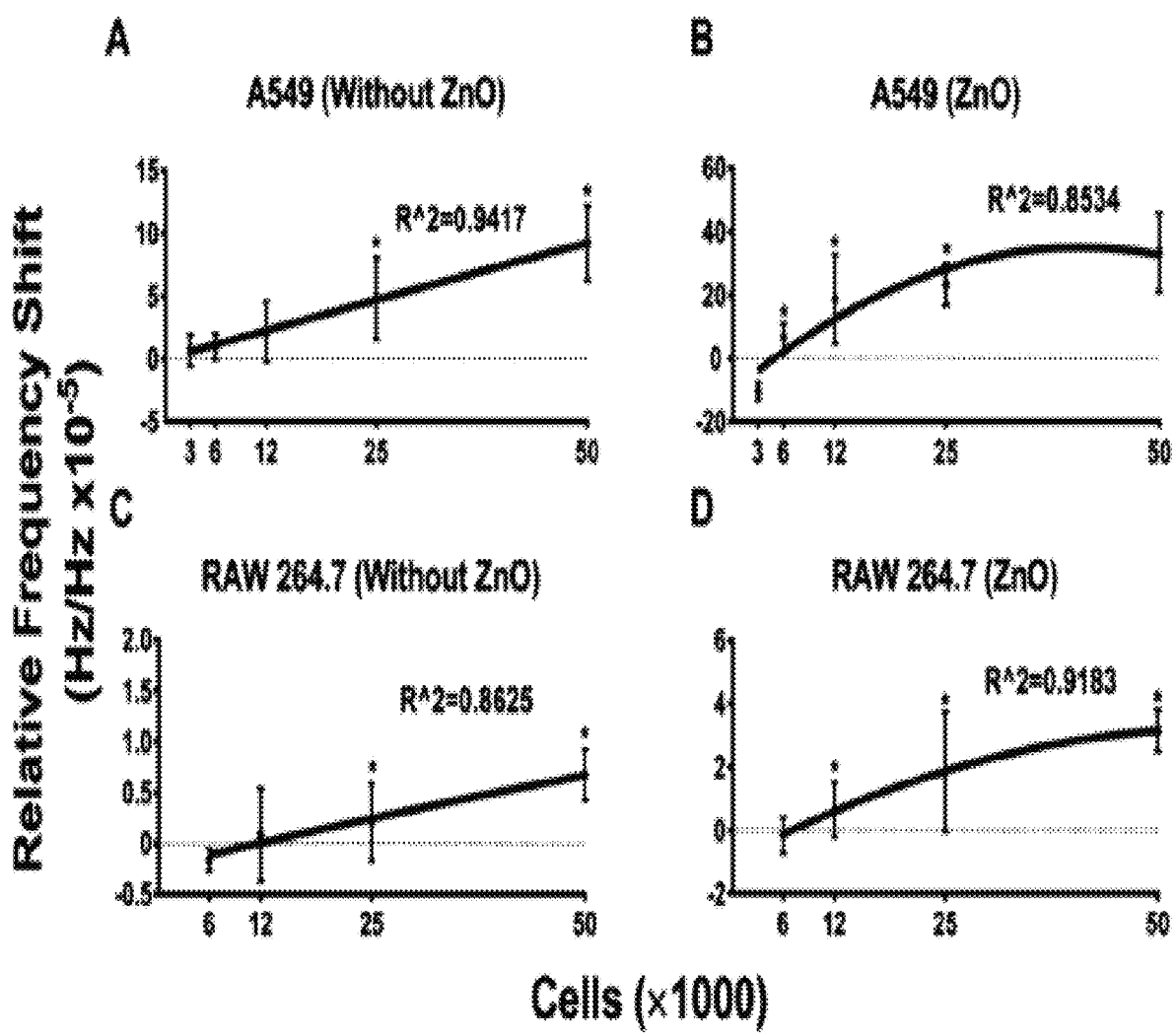
Figure 5A-D

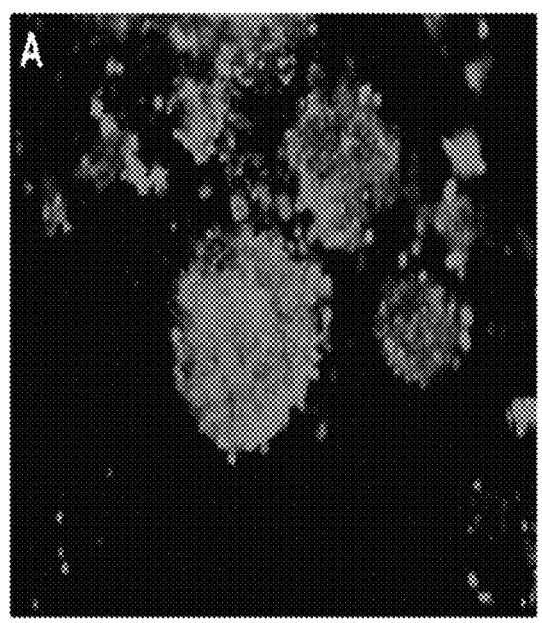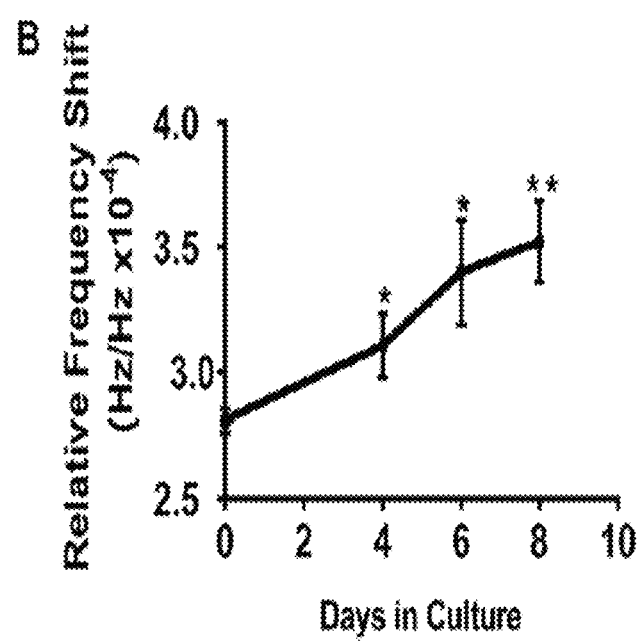
Figure 7A-B

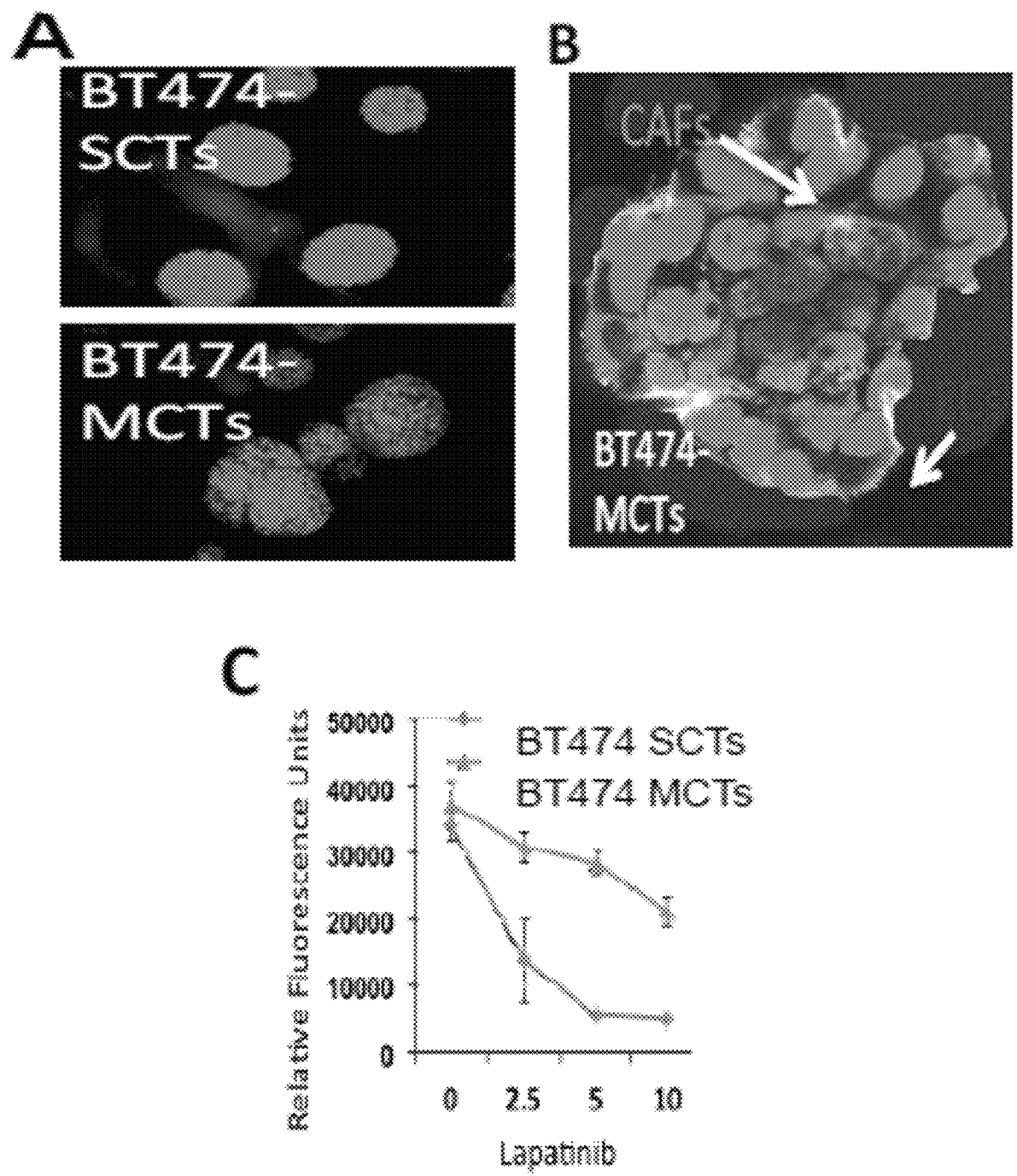
Figure 9A-C

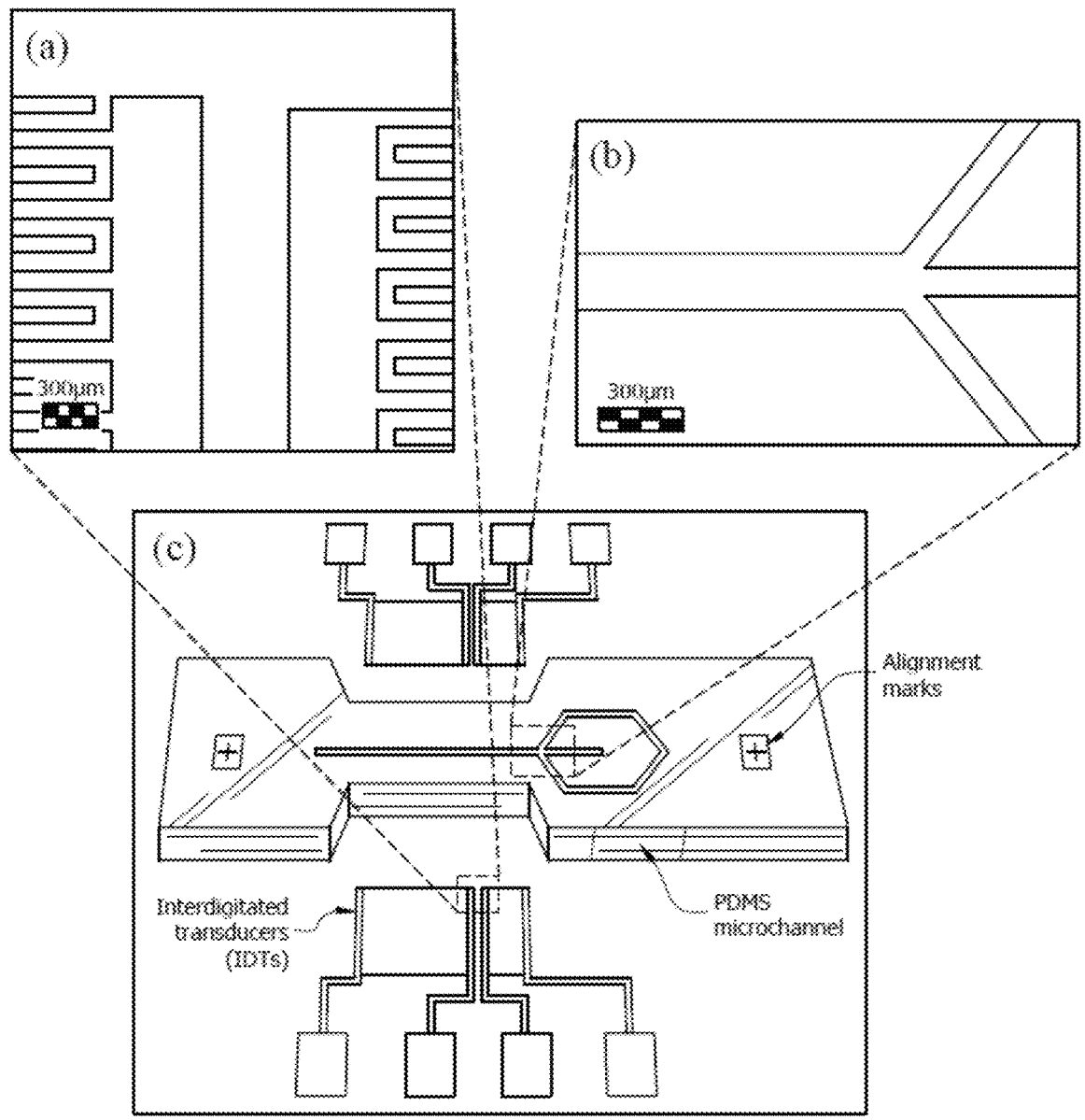
Figure 12A-C

SYSTEM AND METHOD OF MEASURING CELL VIABILITY AND GROWTH

CROSS REFERENCE TO RELATED APPLICATIONS

This application is a divisional of and claims priority to currently U.S. Nonprovisional application Ser. No. 15/682,070, entitled "SYSTEM AND METHOD OF MEASURING CELL VIABILITY AND GROWTH", filed Aug. 21, 2017 now U.S. Pat. No. 10,520,472, which is a continuation of and claims priority to International Patent Application No. PCT/US2016/018762, entitled "SYSTEM AND METHOD OF MEASURING CELL VIABILITY AND GROWTH", filed Feb. 19, 2016 by the same inventors, which claims priority to U.S. Provisional Patent Application No. 62/118,300, entitled "METHOD OF PERFUSED TUMOROID CULTURE DETECTING DRUG EFFICACY", filed Feb. 19, 2015, and U.S. Provisional Patent Application No. 62/252,051, entitled "METHOD OF MEASURING CELL VIABILITY AND USES THEREOF", filed Nov. 6, 2015, the entire contents of each of which is herein incorporated into this disclosure.

GOVERNMENT SUPPORT

This invention was made with Government support under Grant No. R01CA152005 awarded by the National Cancer Institute (NCI). The Government has certain rights in the invention.

FIELD OF INVENTION

This invention relates to devices and methods of measuring cell growth and viability. Specifically, the invention describes a device and method for detection of cell growth and measurement of cancer cell viability.

BACKGROUND OF THE INVENTION

Tumor Systems

Significant challenges remain in the ability to translate fundamental discoveries in cancer biology and genetics into anti-cancer drug discovery and personalized cancer therapy. Given the high failure (>90%) rate of cancer drugs, there was a need for development of a suitable 3D culture system instead of the currently used monolayer (2D) cultures for anticancer drug development.

To overcome these limitations, researchers have turned to 3D in vitro tumor model systems that better replicate the structure, physiology, and function of tissues, and recreate the in vivo morphology and arrangement of individual cells, concentration gradients of signaling molecules and therapeutic agents and the composition, structure, and mechanical forces of extracellular matrix (ECM) around cells. A variety of approaches such as hanging drop, hydrogels, scaffolds, and spinner flask have been developed to create tumor spheroids, considered the best-validated 3D model, however most of these approaches fail to fully recapitulate in vivo tumors.

The best available 3D tumor spheroid systems suffer from a number of problems including long cultivation time, formation of unequal-sized spheroids, and difficult mechanical accessibility. For-instance, hydrogels may create artificial cell-cell or cell-matrix interactions rendering screening of tumor-stroma-interaction-targeting drugs more difficult. The hanging drop method is non-scaffold based, cumbersome, requires more time for epithelial-to-mesenchymal transition (EMT) and does not fully represent the complexity of the in vivo tumor microenvironment (TME). Despite progress in these models, the fact that only ~10% of researchers today use 3D systems underlies the unmet need to develop a more economical, faster, and better in vitro 3D tumor model that more closely mimics the in vivo TME.

The inventors previously developed a novel 3D electrospun polymeric nanofibrous scaffold (PNS) on which cancer cells form tight, irregular aggregates referred to as tumoroids, which exhibit EMT and drug responsiveness, similar to in vivo tumors. (Girard, Y. K. et al. *PLoS One* 8, (2013). PNS can be used to a) develop single cell-line tumoroids (SCTs) or multi-cell tumoroids (MCTs), b) investigate inducible or smart drug release from nanoparticles, and c) the potential to target stromal cells in the TME, which play key roles in drug resistance. Previous research has led to the development of technically simple yet biologically robust PNS-MCTs and -biopsy derived tumoroids (BdTs), which resemble tumors in vivo, and in cancer, can aid in identification of biomarkers of clinical efficacy. The most notable feature of the PNS-MCTs and -BdTs is their characteristic tumor heterogeneity resulting from co-culture of tumor cells with stromal cells, such as cancer-associated fibroblasts (CAFs) and endothelial cells (ECs), the components of TME that participate in inducing drug resistance. However, a major limitation of the PNS-MCT/BdT system is that the data are acquired from PNS-derived MCTs cultured in static media over 7-10 days, which contrasts in vivo conditions, where drugs are in circulation. Also, often parallel wells are used for different time points and dose response studies the data acquired may not provide adequate data due to errors. The static culture conditions distract the tumoroids mimicking in vivo conditions.

Surface Acoustic Wave (SAW) Sensors

Detection and quantification of cell viability and growth in two-dimensional (2D) and three-dimensional (3D) cell cultures commonly involve harvesting of cells and therefore requires a parallel set-up several replicates for time lapse or dose response studies. Currently, cell growth or proliferation of flat 2D cultures utilize MTT assay, flow cytometry and Ki 67 staining. Similarly, measuring cell growth and proliferation in 3D cultures consist of terminal studies that may include trypsinization and staining with trypan blue and quantification. Longitudinal detection of cancer cell viability and growth in 2D and 3D cell cultures in a non-invasive and touch-free fashion remains a major unmet need in research pertaining to cancer cell biology and anti-cancer drug development. The potential application of biosensors for the detection of cell growth has not been reported and remains to be elucidated.

Generally, biosensors such as surface acoustic wave (SAW) are widely used in cancer biomarker detection and bio-agent detection. Gas sensors, biosensors and chemical sensors are a few of the leading applications for surface acoustic wave (SAW) sensors. [(Shen, C. & Liou, S. 131, 673-679 (2008); Onen, O. et al, 12317-12328 (2012); Onen, O. et al. *Sensors (Basel)*. 12, 7423-37 (2012); Vivancos, J.-L. et al, *Sensors Actuators B Chem.* 171-172, 469-477 (2012)] Generally, biosensors are widely used in cancer biomarker detection and bio-agent detection. Due to SAWs' advantages of low cost, small size and ease of assembly, SAW-based biosensor technologies have the potential to transform the cancer and bio-agent detection fields. (Onen, O. et al. *Sensors (Basel)*. 12, 7423-37 (2012); Pomowski, et al. 15, 4388-4392 (2015))

SAWs include two particle displacement components. One is along the direction of wave propagation and the second one is normal to the surface, such as Rayleigh waves. Rayleigh waves, which generate compressional waves, are affected and damped by the liquid loading and dissipate the wave energy into the liquid. Therefore Rayleigh surface acoustic waves are less sensitive to mass loading changes. [(Nomura, T. et al. *Sensors Actuators B Chem.* 76, 69-73 (2001)] Shear horizontal surface acoustic waves (SH-SAWs) with the substrate polarized normal to wave propagation are most commonly used in sensor applications that involve fluidics.

Many different wafer types with special cuts are used for shear horizontal wave excitation, such as ST-cut Quartz and 36° Y-cut LiTaO$_3$. [(Nomura, T. et al. *Sensors Actuators B Chem.* 76, 69-73 (2001); Deobagkar, D. D, et al. 104, 85-89 (2005); Roederer, et al. 2333-2336 (1983); Kondoh, J. et al. 129, 575-580 (2008); Nomura, T., et al. *Sensors Actuators B Chem.* 91, 298-302 (2003)] ST-cut Quartz and 36° Y-cut LiTaO$_3$ are very stable substrates for sensor applications. However, the electroacoustic coupling coefficient ($K^2$) of ST-cut Quartz is much smaller than that of 36° Y-cut LiTaO$_3$ (36° Y-cut LiTaO$_3$ is 4.7 and ST-cut Quartz is 0.0016). [(Litao, Y. et al. *Sensors Actuators A. Phys.* 193, 87-94 (2013)] Because of its high electroacoustic coupling coefficient, the 36° Y-cut LiTaO$_3$ generates more stable signals when the SH-SAWs travel through polydimethylsiloxane (PDMS) which absorbs the majority of the energy generated by the interdigital transducers. [(Shilton, R. J, et al. (2014); Li, F. (ProQuest, UMI Dissertation Publishing (Sep. 4, 2011), 2011] PDMS has been widely used in biomedical devices due to its biocompatibility and ease of manufacture into fluidic channels. An optimization of the PDMS channel sidewall thickness was demonstrated to reduce the damping effect of the PDMS on the wave propagation thereby increasing the sensitivity of the sensor. [(Jo, M. C. & Guldiken, R. *Microelectron. Eng.* 113, 98-104 (2014)]

Even though 36° Y-cut LiTaO$_3$ has a higher electroacoustic coupling coefficient, it also has a higher temperature coefficient compared to the ST-Quartz. Various guide layers can be deposited on the LiTaO$_3$ to change the phase velocity and temperature coefficient of the system. Zinc Oxide (ZnO) is a relatively common material in sensor and SAW fields. The majority of SAW devices coated with ZnO are used as pH or UV sensors. [Oh, H. et al. *Microelectron. Eng.* 111, 154-159 (2013); Chivukula, V. et al. *Appl. Phys. Lett.* 96, 3-6 (2010)] Coating a ZnO layer on a LiTaO$_3$ substrate reduces the temperature coefficient and increases the mass sensitivity, hence addressing the shortcoming of the LiTaO$_3$ substrate as opposed to its alternatives. [Powell, D. A. et al. *Sensor Actuat A-Phys* 115, 456-461 (2004); Powell, D. a., Kalantar-zadeh, K. et al. 2002 *IEEE Ultrason. Symp.* 2002. *Proceedings.* 1, 493-496 (2002); Chang, R.-C. et al. *Thin Solid Films* 498, 146-151 (2006); Fu, Y. Q. et al. *Sensors Actuators B Chem.* 143, 606-619 (2010)]

For effective biosensing there is a dire need for the development of non-invasive and touch-free detection of cancer cell viability and growth or proliferation in three-dimensional (3D) cell cultures as it pertains to assessing clinical efficacy of anti-cancer drugs. Currently a single platform integrating non-invasive biosensing with a perfused MCT platform does not exist. Having a single platform combining microfluidics for perfusion-based nanodrug delivery, acoustic biosensing with real-time physiologic readouts and MCTs with an in vivo TME provides a unique opportunity to study in vivo nanodrug transport and increase the understanding and highly impact drug delivery to cancer cells and estimating the clinical efficacy of anticancer drugs. However, in view of the art considered as a whole at the time the present invention was made, it was not obvious to those of ordinary skill in the field of this invention how the shortcomings of the prior art could be overcome.

SUMMARY OF INVENTION

This invention pertains to the development of an integrated device that incorporates microfluidic-based perfused tumoroid system with SAW-based biosensing method to monitor cell proliferation/growth and prognostic biomarkers in long-term 2D and 3D cell cultures in a non-invasive touch-free manner. To test this biosensing idea, a PDMS channel/well and surface acoustic wave transducers coated with a ZnO layer were utilized to measure mass changes due to increasing cell numbers in normal murine RAW264.7 macrophages and human A549 lung adenocarcinoma cell lines. The results indicate that the novel microfluidic SAW device is capable of monitoring and quantifying cell density of both cell lines in suspension as well as cultured on a 3D-nanofiber scaffold. A model has been developed to integrate this to a microfluidic-based perfused tumoroid model which can be used to detect clinical efficacy of anti-cancer drugs.

In an embodiment, a non-invasive and touch-free method of detecting and quantifying cell growth and viability is presented comprising: providing a shear horizontal-surface acoustic wave device; seeding cells into the Y-shaped microfluidic well; applying a surface acoustic wave (SAW) to the cells; and using a digital frequency counter to count relative frequency response of the cells over a period of time wherein the relative frequency response of the cells over time determines the cell growth and viability. The SH-SAW device can be comprised of two pairs of resonators formed on a lithium tantalite substrate wherein each resonator is comprised of at least one interdigital transducer having at least one pair of reflecting fingers and a Y-shaped microfluidic well formed on each transducer. Each transducer can be coated with a substance selected from the group consisting of zinc oxide (ZnO), silicon oxide (SiO$_2$), silicon nitride (Si3N4), titanium oxide (TiO2), PMMA, Parylene-C and SU-8. The lithium tantalite substrate can be a 36° Y-cut LiTaO$_3$ substrate. The number of reflecting fingers can be 30 pairs. The cells can be obtained from a 2D or 3D cell culture system with the 3D cell culture system using a 3P scaffold to grow tumoroids.

In another embodiment, a shear horizontal-surface acoustic wave device for detecting and quantifying cell growth and viability is presented comprising: two pairs of resonators formed on a lithium tantalite substrate wherein each resonator is comprised of at least one interdigital transducer having at least one pair of reflecting fingers and a Y-shaped microfluidic well formed on each transducer wherein each transducer is coated with a substance selected from the group consisting of zinc oxide (ZnO), silicon oxide (SiO$_2$), silicon nitride (Si3N4), titanium oxide (TiO2), PMMA, Parylene-C and SU-8. The lithium tantalite substrate can be a 36° Y-cut LiTaO$_3$ substrate. The number of reflecting fingers can be 30 pairs with the wavelength of the reflecting fingers being about 297 μm; the height of the reflecting fingers being about 100 nm; the width of the reflecting fingers being about 74.25 μm. In embodiments where the coating is ZnO, the thickness of the ZnO layer can be about 200 nm. The velocity of the surface acoustic wave can be about 4160 m/s and the operation frequency of the device can be about 14.05 MHz.

In a further embodiment, a system for detecting and quantifying cell growth is presented comprising: a SH-SAW biosensor having two pairs of resonators formed on a lithium tantalite substrate, such as 36° Y-cut LiTaO$_3$, wherein each resonator is comprised of at least one interdigital transducer having at least one pair of reflecting fingers coated with zinc oxide (ZnO) and a Y-shaped microfluidic well formed on each transducer; a syringe pump to precisely manipulate liquid into microfluidic channels of the SH-SAW biosensor; a signal generator connected to the SAW biosensor wherein the signal generator generates a signal to the SH-SAW biosensor; two RF amplifiers connected to the SH-SAW biosensor wherein the amplifiers optimize oscillator circuit loop gain; a digital frequency counter connected to the SH-SAW biosensor wherein the digital frequency counter quantifies the frequency shift; a band pass filter connected to the amplifiers; an oscilloscope to visualize frequency shift and oscillation in real-time; and a computer processor to record data. The number of reflecting fingers on the SH-SAW biosensor can be 30 pairs or more.

BRIEF DESCRIPTION OF THE DRAWINGS

For a fuller understanding of the invention, reference should be made to the following detailed description, taken in connection with the accompanying drawings, in which:

FIG. 3A-B depicts cell viability following SAW measurement. Immediately following SAW measurement the viability of (A) A549 and (B) RAW 264.7 cells was determined by trypan blue exclusion. Data is plotted as mean±SEM. The data is a representative of a study that was performed in triplicates and performed at least two independent times. A student's t-test was used to evaluate significance (* $p \leq 0.05$, when compared to control).

FIG. 4A-C depicts cell proliferation following SAW measurement. Immediately following SAW measurement A549 cells were seeded onto a 96 well plate at a density of 5,000 cells per well. Representative images of control and tested groups are shown: (A) A549 cells 72 hr after SAW test, (B) NucBlue staining of A549 cells 72 hr after test, and (C) Control cells after 72 hr.

FIG. 5A-D depicts a relative frequency shift response to the different cell concentrations. (A) The bare SAW resonator response to A549 cell with concentration of 3K, 6.25K, 12.5K, 25K and 50K in 100 μl media for each test. (B) The SAW resonator coating with ZnO layer response to A549 cells. (C) The bare SAW resonator response to RAW 264.7 cell concentration (D) The relative frequency shift response to RAW 264.7 cell concentration with ZnO layer. Data is plotted as mean±SEM. The data is a representative of a study that was performed in triplicates and performed at least two independent times. A student's t-test was used to evaluate significance ($p \leq 0.05$). * indicates a significant difference in the frequency shift between the labeled group and the adjacent lower concentration. Best fit curves were calculated using a second order polynomial model in the GraphPad Prism software application.

FIG. 7A-B is a representative image of A549 cells growing in 3D tumoroid structures on the 3P scaffold using NucBlue nuclear stain on day 8 of culture. In FIG. 7B, A549 cells were cultured on the 3P scaffold for 8 days. On days 0 (scaffold with no cells), 4, 6, and 8 scaffolds were collected and transferred to the SAW device with ZnO layer for measurement. Data is plotted as mean±SEM. The data is a representative of a study that was performed in triplicates. *=significant increase from day 0 **=significant increase from day 4 ($p \leq 0.05$).

FIGS. 9A-C are a series of images depicting growth of BT474 derived SCTs (A) and MCTs (B) for 6 days on PNS; tumoroids are stained with calcein AM/EthD-1. Confocal (merged z-stacked) images showing presence of ECs (vWF, green cells), CAFs (SMA positive, red cells) and DAPI (cell nuclei) in BT474-MCTs imaged by confocal microscopy (merged z-stacked images). (C) Differential response of BT474-SCTs and -MCTs to lapatinib. On day 2 after co-culture, BT474 cells were treated with increasing concentrations (μM) of lapatinib for 72 h; cell viability was measured by PrestoBlue assay.

FIG. 12A-C are a series of images depicting a schematic of fully integrated designed, fabricated acoustic microfluidic chip, with channel mold before bonding and interdigitated transducers at the Inventors' Labs. a) Close-up of the interdigitated transducers, b) Microfluidic channel mold before bonding c) Completed fully-integrated acoustic based microfluidic chip.

DETAILED DESCRIPTION OF THE PREFERRED EMBODIMENT

Figure 1A:
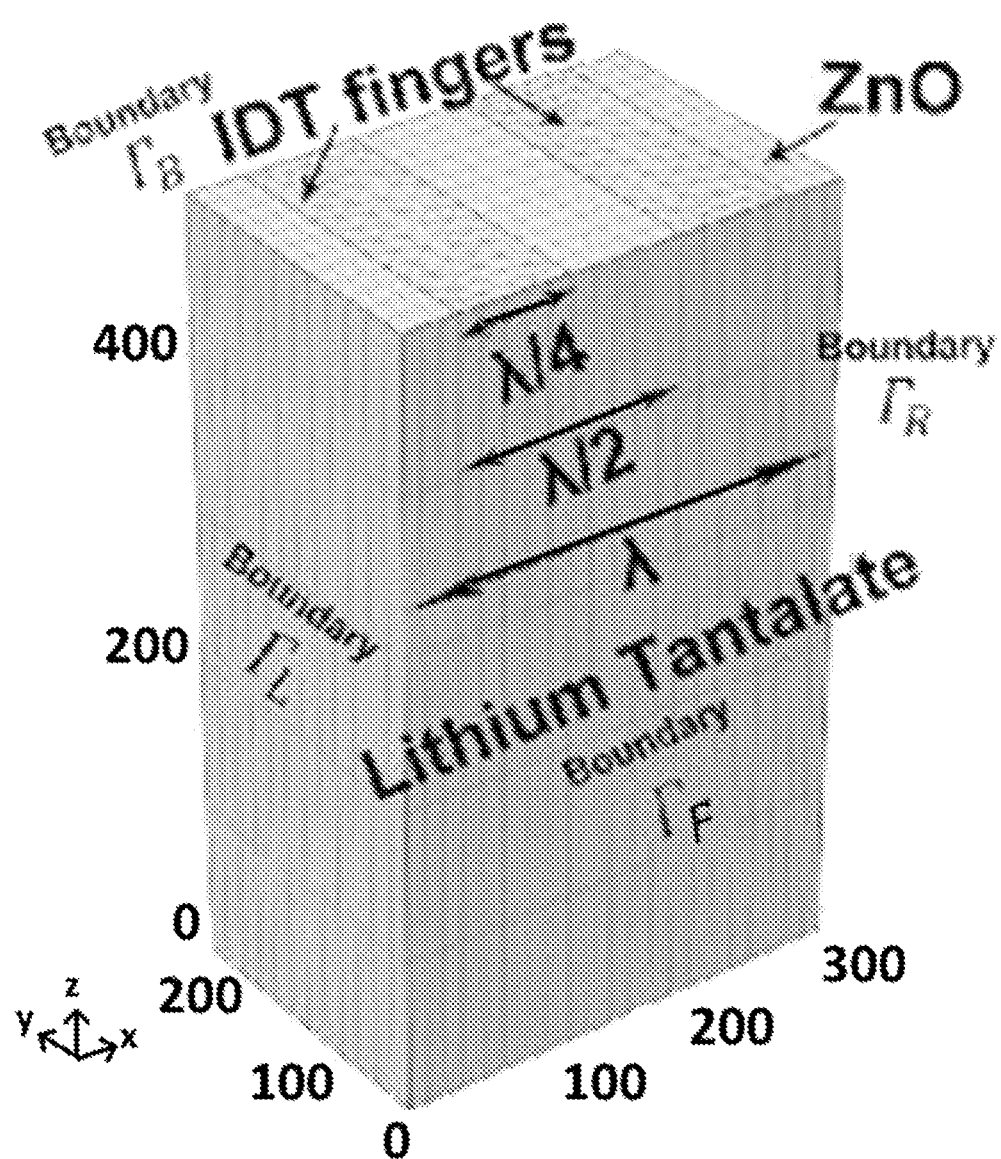
FIG. 1A depicts a 3D COMSOL model and simulation results based on the 36° Y-cut LiTaO3. (A) 3D cell model geometry with mesh.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise.

"Surface acoustic wave (SAW) biosensor" as used herein refers to a biosensor which produces surface acoustic waves (SAW). The SAW biosensor as disclosed herein can be formed from a piezoelectric substrate including, but not limited to, lithium tantalate such as 36° YX lithium tantalate. A number of additional substrates can be used including 36° Y-cut LiTaO$_3$ (Lithium Tantalate), ST-cut Quartz, 36° Y-Cut Quartz, 41° Y-cut LiNbO3 (Lithium Niobate), 64° Y-cut LiNbO3 and other similar substrates. The SAW biosensor can be comprised of at least two pairs of interdigital transducers having a plurality of reflecting fingers. In some embodiments the number of reflecting fingers is about 30 pairs, but there is no theoretical limitation for maximum number of transducers. The maximum number of transducers is limited by the available space on the designed chip. In another embodiment, the interdigital transducers are coated with zinc oxide (ZnO). While ZnO is used in the examples presented herein, the type of coating can also include, but is not limited to, SiO$_2$ (silicon oxide), Si3N4 (silicon nitride), TiO2 (Titanium oxide), PMMA, Parylene-C and SU-8.

"Nanofiber scaffold" as used herein refers to a 3D cell culture system in which a 3D nanofibrous scaffold is used that is produced by electrospinning a mixture of poly(lactic-co-glycolic) (PLGA) and a block copolymer of polylactic acid (PLA) and mono-methoxypolyethylene glycol (mPEG)

designated as 3P. The 3P scaffold is used to form tight irregular aggregates called "tumoroids" which are similar to in vivo tumors.

Acoustic biosensing involves a highly sensitive and tunable surface acoustic wave (SAW), which can be performed without any electrode with or without touching the PNS. Acoustical response can be acquired independent of existence of a magnetic/electrical field and iron oxide/MnO nanoparticles in the flow field. Since surface acoustic waves (SAWs) permit mass loading-based biosensing, the potential of SAW-biosensing to detect and quantify cell growth was examined.

The inventors determined that a shear horizontal (SH)-SAW device comprising two pairs of resonators including interdigital transducers and reflecting fingers can be used to quantify mass loading by cells in suspension as well as within a 3D cell culture platform. A 3D COMSOL model was built to simulate the mass loading response of increasing concentrations of cells in suspension in the polydimethylsiloxane (PDMS) well in order to predict the characteristics and optimize the design of the SH-SAW biosensor. The simulated relative frequency shift from the two oscillatory circuit systems (one of which functions as control) were found to be concordant to experimental data generated with RAW.247 macrophage and A549 cancer cells. Also, results showed that SAW measurements per se did not affect viability of cells. Further, SH-SAW biosensing was applied to A549 cells cultured on a 3D electrospun nanofiber scaffold that generate tumor spheroids (tumoroids) and the results showed the device's ability to detect changes in tumor spheroid growth over the course of eight days. Taken together, these results demonstrate the use of SH-SAW device for detection and quantification of cell viability changes over time in 2D suspension cultures and in 3D cell culture models, which may have potential applications in both longitudinal 3D tumoroid cell cultures in cancer biology and in regenerative medicine. Specifically, the SH-SAW device could be used to (a) monitor cell viability in cancer cells after treatment with an novel anti-cancer agent, (b) study kinetics of anti-cancer drug-induced cell death in cancer cells thus aiding in drug discovery, (c) study the cell proliferation capacity of cancer cells, and (d) monitor xenotoxicity in cell cultures to be used in regenerative medicine, (e) measure drug efficacy of chemotherapies in biopsy- or tumor tissue-derived tumoroids thus providing evidence for the most effective treatment for that individual cancer patient.

Currently, 3D tumoroids are cultured in 96 well plates for 6 days with media changes on days 2 and 4. To imitate this in the microfluidic system, in one embodiment, the inventors fabricated a 4-well chamber with 6.35 mm diameter (i.e. equivalent of a well in 96-well plate), which allows sampling data from 4 replicates at a time. The system consists of a syringe pump (to precisely manipulate liquid in the microfluidic channels), two RF amplifiers (to optimize the oscillator circuit loop gain), a digital frequency counter (to quantify the frequency shift), a custom-designed passive filter (to optimize the oscillator circuit loop phase) and an oscilloscope (to visualize the frequency shift and oscillation real-time).

The fabricated interdigitated transducer pairs are used as the feedback element of the amplifiers. The quantifiable output (frequency shift) are displayed by a frequency counter and a connected computer records data. Also, the perfusion conditions are established with an appropriate flow rate (low vs high) to mimic media changes on days 2 and 4.

Ongoing experiments are undertaken to compare the tumoroid formation in static (as control) vs. perfusion culture on days 6 and 10.

Figure 11A:
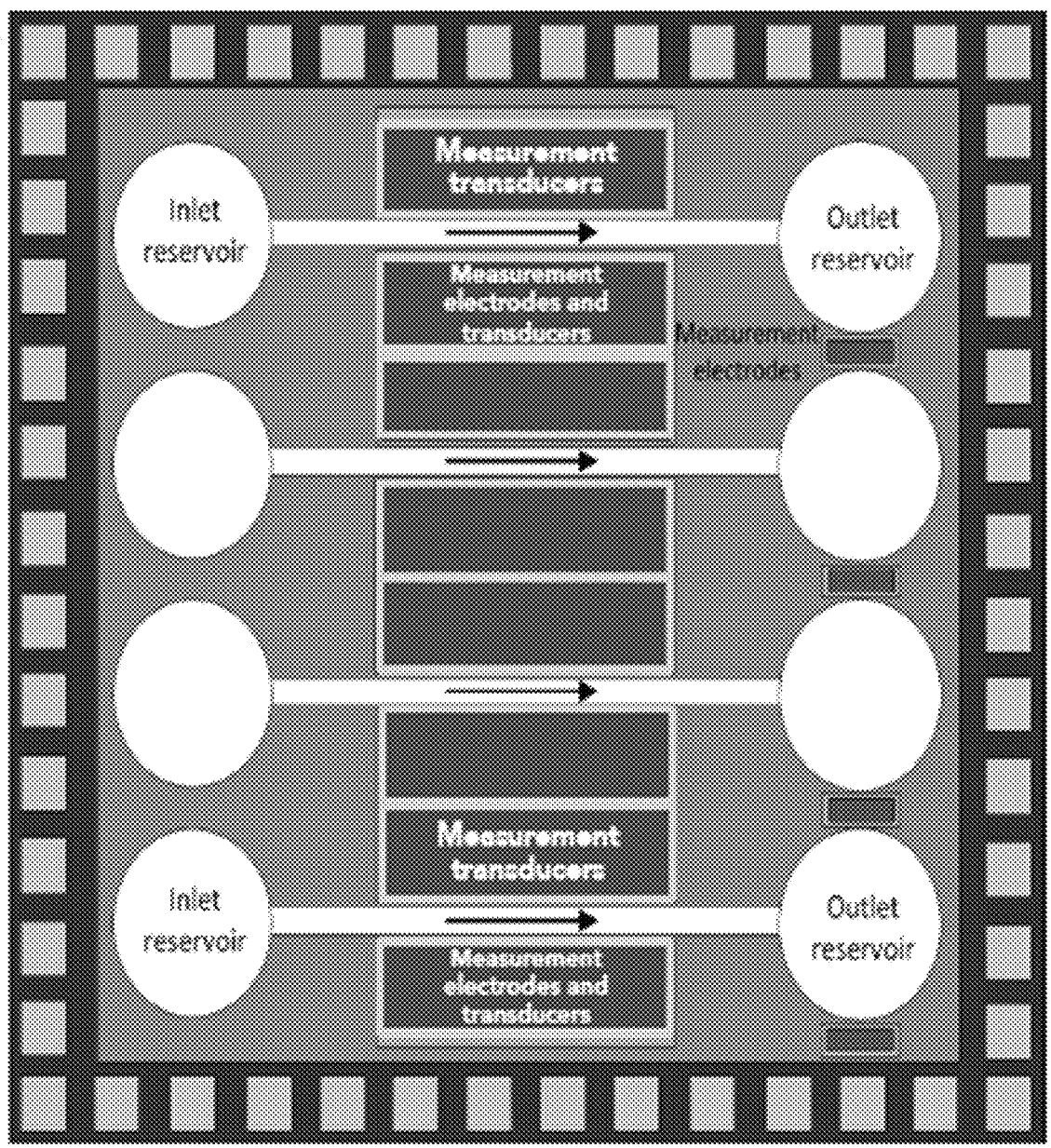
FIG. 11A is an image depicting the conceptual overall zoomed-in view of a single unit cell in the microfluidic chip proposed on an interfacing electronic board to investigate physiological changes in tumor cells. Arrows indicate fluid flow direction. Drawing is not to scale.
Figure 11B:
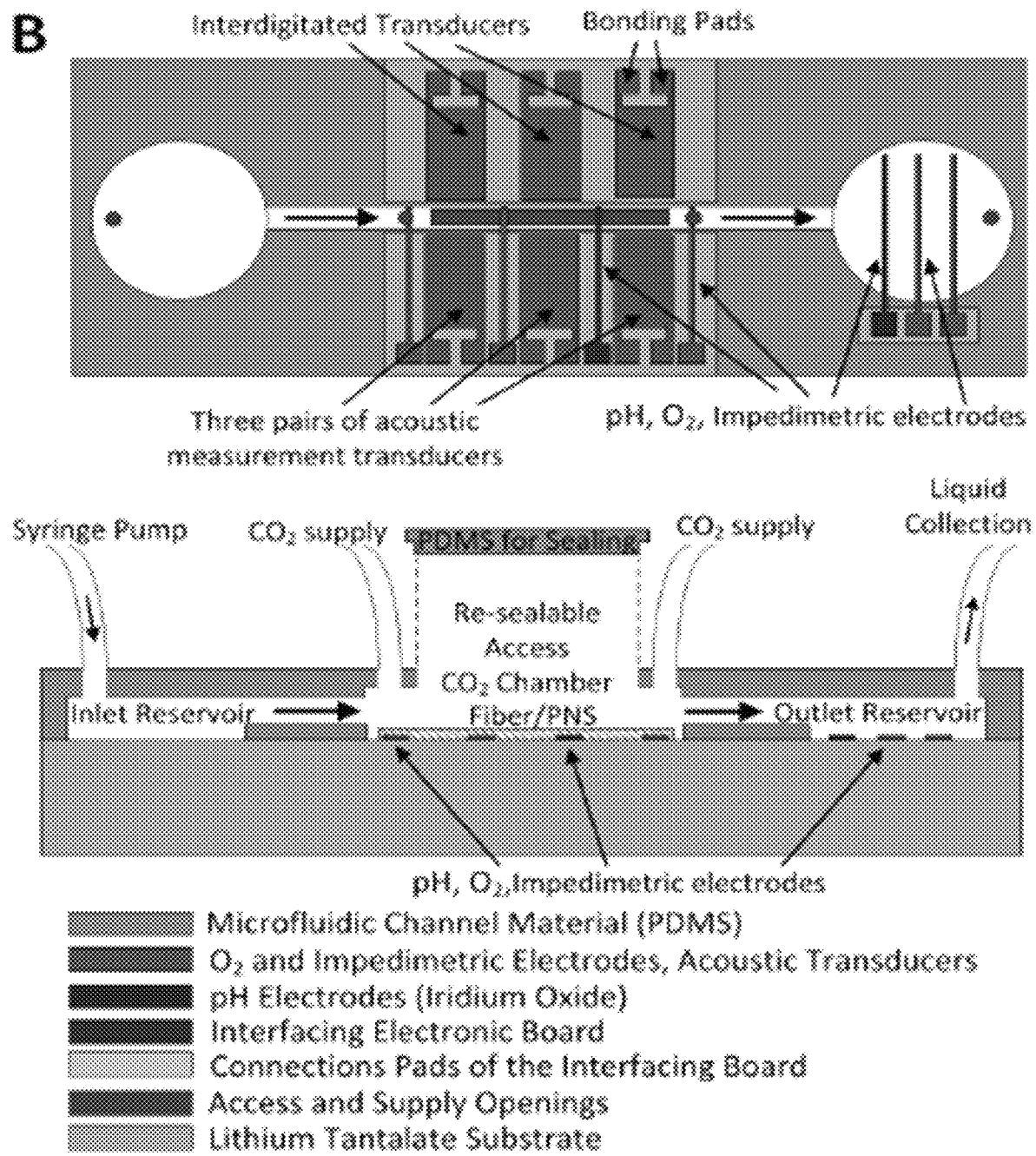
FIG. 11B is an image depicting top and side views of a single unit cell in the microfluidic chip proposed on an interfacing electronic board to investigate physiological changes in tumor cells. Arrows indicate fluid flow direction. Drawing is not to scale.

The procedures to fabricate the microfluidic chip for one embodiment, included: depositing and patterning a thin titanium (for promoting adhesion) and gold layer on a double-sided polished 36° YX lithium tantalate substrate with a DC sputter. The layer patterned by a single mask formed the O2, impedance measurement and interdigitated electrodes. A microfluidic channel and reservoir were then fabricated using soft lithography and replica molding techniques. The mold of the microfluidic channel was fabricated on a silicon wafer with SU-8, epoxy-based negative photoresist and the PDMS prepolymer base was cross-linked with curing agent (Sylgard™ 184 kit) in a weight ratio of 10:1, poured onto the fabricated SU-8 microfluidic channel mold, and then cured. A resealable access opening was formed on the mold during this fabrication step. This was followed by surface functionalization, placing the 3PNS on the substrate containing the transducers and generating inlet, outlet and CO2 access holes prepared using a 0.75 mm biopsy punch and for acoustical measurement. The final step of the fabrication is bonding of the PDMS microchannel to the substrate containing pH, O2, impedance measurement and interdigitated electrodes, and 3D nanofiber scaffold. A schematic of this embodiment of the microfluidic system is shown (FIG. 11).

In an embodiment, the current invention includes an SH-SAW biosensor with two pairs of resonators, including interdigital transducers reflecting fingers to quantify mass loading by the cells in suspension as well as within a 3D cell culture platform. The results of relative frequency shift from the two oscillatory circuit systems (one of which functions as control) were compared to experimental data generated by increasing cell concentrations in the polydimethylsiloxane (PDMS) well. The results showed that SAW measurements per se did not affect viability of cells and could be used to determine cell growth in non-cancerous and cancerous cell line. Frequency shift measurements were also applied to A549 cells cultured on a 3D electrospun nanofiber scaffold and the results showed the device's ability to detect changes in tumor spheroid growth over the course of eight days. Taken together, these results demonstrate the biocompatibility of SAW and its ability to detect changes in cell density over time in suspensions and in 3D cell culture model, which may have potential applications in both longitudinal in vitro 2D and 3D cell cultures in anti-cancer drug discovery and development.

Design of Bio-Sensor

Figure 1B:
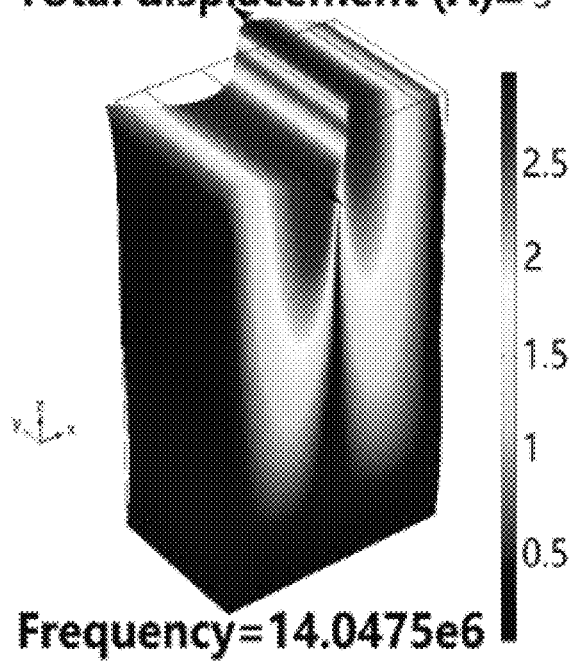
FIG. 1B depicts a 3D COMSOL model and simulation results based on the 36° Y-cut LiTaO3. (B) Resonance frequency of the IDTs with a 200 nm thick ZnO layer.
Figure 1C:
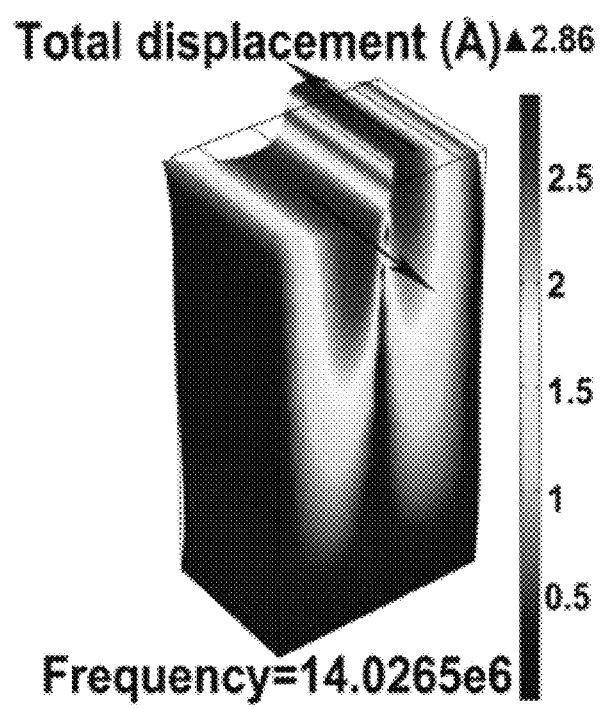
FIG. 1C depicts a 3D COMSOL model and simulation results based on the 36° Y-cut LiTaO3. (C) Resonance frequency of the IDTs with 12.5 K cells media on the 200 nm thick ZnO layer surface.

A 3D COMSOL model that includes a two-port resonator was built to characterize changes to the wave propagation characteristics resulting from alterations to mechanical properties inside the well. A simplified 3D cell model of the Lithium tantalate resonator was built to obtain the resonator frequency shifts by the eigen frequency module of the COMSOL software. Briefly, first, a 300 μm (L)×200 μm (W)×500 μm (H) 3D cell model was created. A pair of 100 nm fingers were modeled on the surface. Then a 200 nm thickness ZnO film was added to the design. A Rotated Coordinate System was set up to specify the orientation of polling direction which was applied to the piezoelectric material substrate. Periodic boundary conditions were applied to the left and right edges to simulate infinite pairs of transducers with this simple model. Linear elastic material was applied to ZnO layer and electrical material model was applied to the pair of fingers. Then a mass loading added to ZnO layer corresponding to various concentrations of cell. A tetrahedral mesh was applied on the model with minimum element size of 0.8 µm. The surface wave was excited by applying 1V of electric potential on one finger while the other finger was connected to the ground. The individual 3D cell was set as periodic to simulate the entire SAW sensor with a fairly-simplified geometry. FIGS. 1A-C illustrate one wavelength cell of the simulated design with interdigital transducers (IDTs). Two interdigital transducer fingers are illustrated where one of them was connected to the ground.

After the model was built and material properties were applied, a mesh was created with total degrees of freedom of 679924. The mesh included 111679 domain elements, 28942 boundary elements and 2892 edge elements. 36° Y-cut $LiTaO_3$ with or without a ZnO coating was employed as the choice of substrate to simulate the resonator frequency. The simulation results indicated that the operation frequency would be 14.0475 MHz without ZnO while the fabricated operation frequency was experimentally measured as 14.056 MHz. The simulation result of the 3D-cell with ZnO is 14.03296 MHz while the experimentally measured value is 14.04120 MHz, illustrating the validity of the developed simulation designs. As expected, the shear horizontal wave propagated in the x direction with the substrate polarized in they direction as illustrated in FIGS. 1B and 1C. Additional device design details are given in Table 1.

TABLE 1

| PARAMETERS | SETTINGS |
| --- | --- |
| Wavelength (λ) | 297 µm |
| Number of Reflecting Fingers | 30 Pairs |
| Finger Width | 74.25 µm |
| Wavelength of Reflecting Fingers | 297 µm |
| Number of Fingers | 30 Pairs |
| Well Diameter | 6.5 mm |
| SAW Velocity | 4160 m/s |
| ZnO layer thickness | 200 nm |
| Finger Heights | 100 nm |
| Operation Frequency | 14.05 MHz |

Device Fabrication

The IDTs were fabricated by the traditional micro-lithography methods while the microfluidic well was fabricated by the conventional PDMS micro molding technique. The IDTs were fabricated using a photolithography process in which a chrome layer of 100 nm thickness was first deposited on a double-side polished 36° Y-cut LiTaO3 wafer with DC sputter. The 36° Y-cut LiTaO3 wafer was then coated with S1813 photoresist of 1.6 µm-thick patterned using a UV light source and developed in MF 319 developer. The chrome layer was then etched with CR-7S chrome etchant and subsequently the photoresist was removed with AZ-400T photoresist stripper. Further details on the fabrication process can be found in the inventors' recent reports, herein incorporated by reference into this application. (Guldiken, R. et al. *Sensors* (*Basel*). 12, 905-22 (2012); Jo, M. C. & Guldiken, R. *Sensors Actuators A Phys.* 187, 22-28 (2012); Jo, M. C. & Guldiken, R. Dual. *Sensors Actuators A Phys.* 196, 1-7 (2013)) Briefly, a lithium tantalate substrate (36° Y-cut LiTaO3) was selected for the substrate of the device.

After the IDTs were fabricated on the lithium tantalate substrate, ZnO sputtering was carried out. A 200 nm thick ZnO film was deposited at 150° C. in two and a half hours. After the ZnO deposition, the PDMS well was bonded to the lithium tantalate substrate after being exposed to 30 seconds oxygen plasma for increased bonding.

The soft lithography and replica molding techniques were used to fabricate the Y-shape microfluidic channel. The mold of the microfluidic channel was fabricated on a silicon wafer with SU-8 negative photoresist of 80 µm-thick. The PDMS pre-polymer base was cross-linked with the curing agent in a weight ratio of 10:1, poured onto the fabricated SU-8 microfluidic channel mold, and then cured at 80° C. for 30 min. Once PDMS replica was peeled off from the microfluidic channel mold, the inlet and outlet holes were generated using 0.75 mm biopsy punch. The surfaces of PDMS replica and the substrate including IDTs were then treated with oxygen plasma for 30 s with 20 sccm oxygen flow rate, 500 mTorr chamber pressure, and 50 W power to increase the bonding strength. Lastly, the PDMS replica of the microfluidic channel was bonded to the substrate including IDTs. (Jo, M. C. & Guldiken, R. *Sensors Actuators A Phys.* 196, 1-7 (2013))

The SAW resonator can be used as a propagation delay-line with a pair of IDT transducers that serve to excite and receive the acoustic wave. Therefore a custom-designed oscillatory circuit system was used for quantifying the cell concentrations as shown in the view in FIG. 2A. Briefly, in the oscillator circuit detection system, the resonator device was used as the feedback element of the RF amplifier. The relative change of SAW velocity due to mechanical and electrical changes led to an oscillation frequency shift. These changes in oscillation frequency were detected with a digital frequency counter, which accurately quantifies the acoustic wave frequency shift. The setup used two variable gain RF amplifiers (Olympus 5073PR and Olympus 5072PR, Olympus NDT Inc., Waltham, Mass., USA), a digital frequency counter (Agilent 53220A, Agilent Technologies Inc., Santa Clara, Calif., USA) and an oscillator (Tektronix TDS2001C, Tektronix Inc., Beaverton, Oreg., USA). A frequency counter and an oscilloscope were connected to the loop by a T connector. The oscilloscope is employed to monitor the phase angle of the both loops (test and control group).

The setup in the control group and test group is the same. Both two-port resonators were connected to the frequency filter on one side and then were connected to amplifier on another side (as this is a closed-loop system, there is no input side or output side). Hence, the surface waves with desired frequency passed the resonator and signal was amplified by the amplifier. This method as intended to reduce undesirable frequency peaks and phase noise in the loop.

Compared to other detection methods, such as a vector voltmeter or network analyzer, an oscillatory circuit configuration was selected due to higher sensitivity and stability. The novel aspects as opposed to prior studies are 1) existence of custom-designed filter in the setup (to eliminate frequencies below 5 MHz and above 20 MHz in the loop) and 2) frequency mixing (test and control group) by frequency counter at high sampling rate.

Figure 2A:
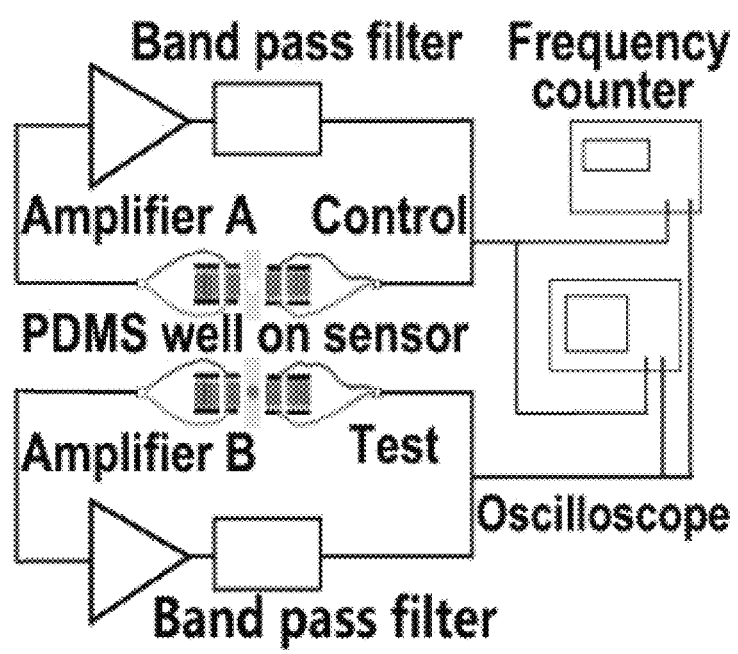
FIG. 2A is a schematic of the oscillatory circuit system. Two resonators with custom-designed oscillatory circuit system were used with one of them as control group.

For the designing, first a 300 µm (L)×200 µm (W)×500 µm (H) 3D cell model was created. A pair of 100 nm fingers were modeled on the surface. Then a 200 nm thickness ZnO film was added to the design. A Rotated Coordinate System was set up to specify the orientation of polling direction which was applied to the piezoelectric material substrate. Periodic boundary conditions were applied to the left and right edges to simulate infinite pairs of transducers with this simple model. Linear elastic material was applied to ZnO layer and electrical material model was applied to the pair of fingers. Then a mass loading added to ZnO layer corresponding to various concentrations of cell. A tetrahedral mesh was applied on the model with minimum element size of 0.8 µm. The surface wave was excited by applying 1V of electric potential on one finger while the other finger was connected to the ground. The fabricated and assembled resonator and fluidic well is seen in FIG. 2A. Compared to other detection methods such as network analyzer, an oscillatory circuit was employed as it offers higher stability as well as higher sensitivity. (Onen, O. et al. *Sensors (Basel)*. 12, 7423-37 (2012); Rocha-Gaso, M.-I. et al. *Sensors (Basel)*. 9, 5740-69 (2009))

In the oscillator circuit detection system, the SAW sensor was employed as the feedback element of the RF amplifier. The relative change of SAW velocity due to mechanical and electrical changes resulted in an oscillation frequency shift. These changes in oscillation frequency were detected with a digital frequency counter. The setup used two variable gain RF amplifiers (Olympus 5073PR and Olympus 5072PR, Olympus NDT Inc., Waltham, Mass., USA), a digital frequency counter (Agilent 53220A, Agilent Technologies Inc., Santa Clara, Calif., USA), an oscillator (Tektronix TDS2001C, Tektronix Inc., Beaverton, Oreg., USA). (Onen, O. et al. *Sensors (Basel)*. 12, 7423-37 (2012)) A band pass filter was used on the amplifier to eliminate the frequencies lower than 5 MHz and higher than 20 MHz in the loop. The two oscillation loops were employed to minimize the background noise and relate the frequency shift to the mass loading of different cell concentrations. A constant volume of different cell concentrations media was supplied to the well in the test loop for each experiment.

During the experiments, the frequency changes for the test group while the frequency of the control group remained nearly constant. From the perturbation theory, when the surface acoustic waves propagates thru the detection area of the sensor, the phase velocity changes due to mass loading from the cell media. In the equation 3 and 4 presented below, $V_1$ is the surface wave phase velocity of the control group device and $V_2$ is the surface wave phase velocity of the actual tested device. $V'_2$ represents the phase velocity of the surface acoustic wave travelling through different cell concentrations. During the experiments, the only real time relative frequency $$\frac{\Delta V}{V} = \frac{V_2 - V'_2}{V_1} \text{ and } \frac{\Delta f}{f} = \frac{\Delta V}{V} = \frac{f_2 - f'_2}{f_1}$$

recorded by the frequency counter. Then the data was sorted by MATLAB and plotted out in normalized relative frequencies.

$$\frac{f_2}{f_1}$$

In one embodiment, fabrication of the microfluidic chip shown in FIG. 11 is conducted in three major steps. The first step involves fabrication of acoustic electrodes for pH, O2, glucose and lactate; impedance measurement electrodes for cell proliferation; and interdigitated electrodes on the substrate for biomarkers. A thin titanium (for promoting adhesion) and gold layer is deposited and patterned on a double-sided polished 36° YX lithium tantalate substrate with a DC sputter (USF cleanroom). The layer patterned by a single mask will form the O2, impedance measurement and interdigitated electrodes.

Second, a microfluidic channel and reservoir is fabricated using soft lithography and replica molding techniques. The mold of the microfluidic channel is fabricated on a silicon wafer with SU-8, epoxy-based negative photoresist. The PDMS pre-polymer base is cross-linked with curing agent (Sylgard™ 184 kit) in a weight ratio of 10:1, poured onto the fabricated SU-8 microfluidic channel mold, and then cured. A re-sealable access opening is formed on the mold during this fabrication step.

The third step is surface functionalization, placing the PNS on the substrate containing the transducers and generating inlet, outlet and CO2 access holes. PNS is precisely placed using alignment marks patterned on the substrate in the chrome deposition step. Surface functionalization is performed in this step for acoustical measurement. Alignment marks assist in functionalizing the specific microchannel location before bonding the channel to the substrate. The inlet/outlet/CO2 access ports is prepared using a 0.75 mm biopsy punch.

The final step of the fabrication is bonding of the PDMS microchannel to the substrate containing pH, O2, impedance measurement and interdigitated electrodes, and fiber scaffold. The surfaces of PDMS replica and the substrate including IDTs is treated with oxygen plasma to increase the bonding strength.

Cell Viability and Proliferation not Affected after SAW Measurements

It was a concern that the cellular stress due to seeding of the cells in the current device followed by exposure to acoustic waves would have a negative impact on the cells' viability and their ability to proliferate. To demonstrate the procedure's innocuous nature and thus its utility in translational lab setting, cell viability was determined. The viability of both normal (RAW 264.7) and cancerous (A549) cells was tested immediately following SAW measurement by trypan blue exclusion. Three replicates were tested for each concentration of both cell lines. A student's t-test was used to determine any significant difference in viability between each pair of control and SAW tested groups. A p-value ≤0.05 was considered to be significant. As seen in FIG. 3, out of the 12 groups compared, only one showed any significant difference in viability.

Next, the long-term effect of the SAW measurement on cell proliferation was observed by performing a re-plating assay as described earlier. Briefly, A549 cells were collected and then seeded onto a 96 well culture plate after SAW measurements. As seen in FIGS. 4A-C, A549 cells exposed to SAW (FIG. 4A) and control untested cells which were not exposed to the SAW device (FIG. 4C) reveals no obvious changes to cell morphology or growth rate after 72 hr. The nuclear staining in FIG. 4B shows that cells have in-tact nuclei and appear healthy.

Frequency Shift Increases with Increasing Cell Concentration and Sensitivity is Further Aided by the Use of ZnO Once it was confirmed that the current bio-sensing device and measurement protocol was bio-compatible, the next step was to determine the sensitivity of the device in accurately measuring cell concentrations. Two variations of the device were used—one that was coated with ZnO and another that was kept bare. The SAW measurement protocol for both the devices was kept constant as described in the experimental setup section. Both the non-cancerous (RAW 264.7) and cancerous (A549) cells were examined in the devices at 6250, 12500, 25000 and 50,000 cells per 100 μL. The concentration of cells were chosen based on cell density that would be encountered when performing actual research studies. As seen in FIGS. 5A-D, a cell dependent increase in the frequency shift was observed in both the cell lines tested. Interestingly, the layer of ZnO increased the sensitivity of the device in recording changes in cell numbers in both of the cell lines tested. Specifically, comparing sensors containing the ZnO layer (FIGS. 5B and D) to those with the bare substrate (FIGS. 5A and C) revealed that the ZnO layer increased the relative frequency response by 4 times which means it increased the sensitivity of the device.

SAW Measurements of Cell Density Match Simulation Results

Figure 2B:
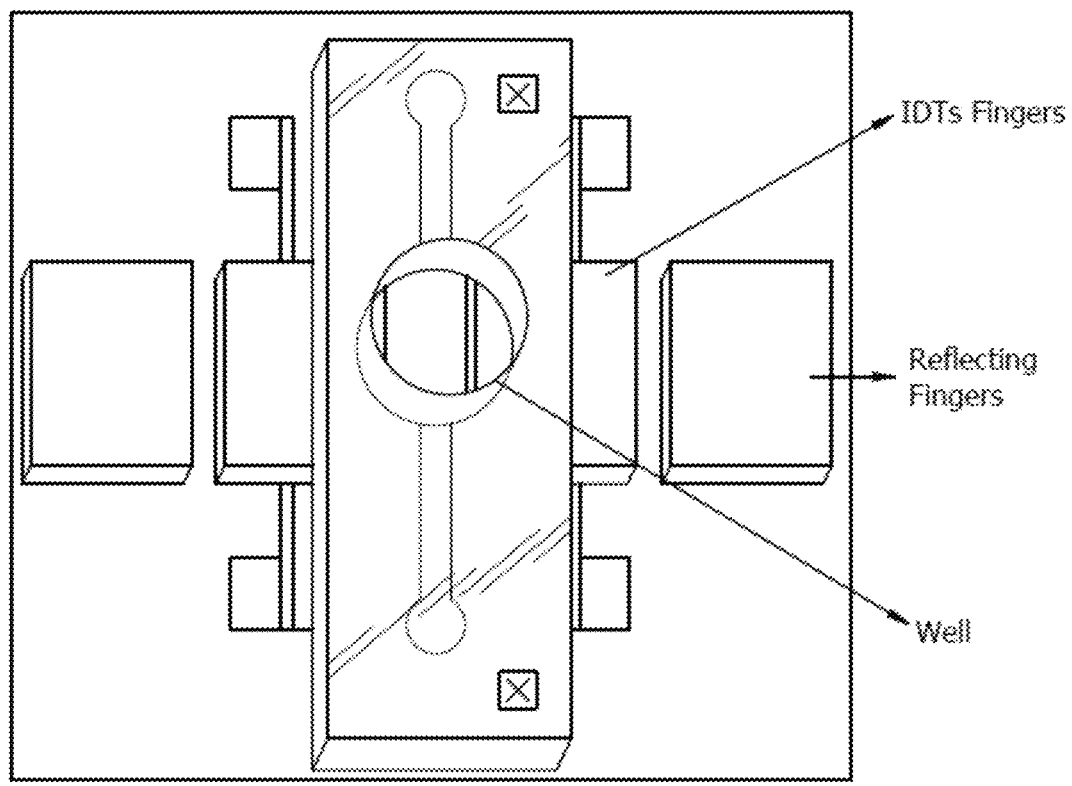
FIG. 2B depicts the fabricated and assembled resonator and fluidic well.
Figure 6:
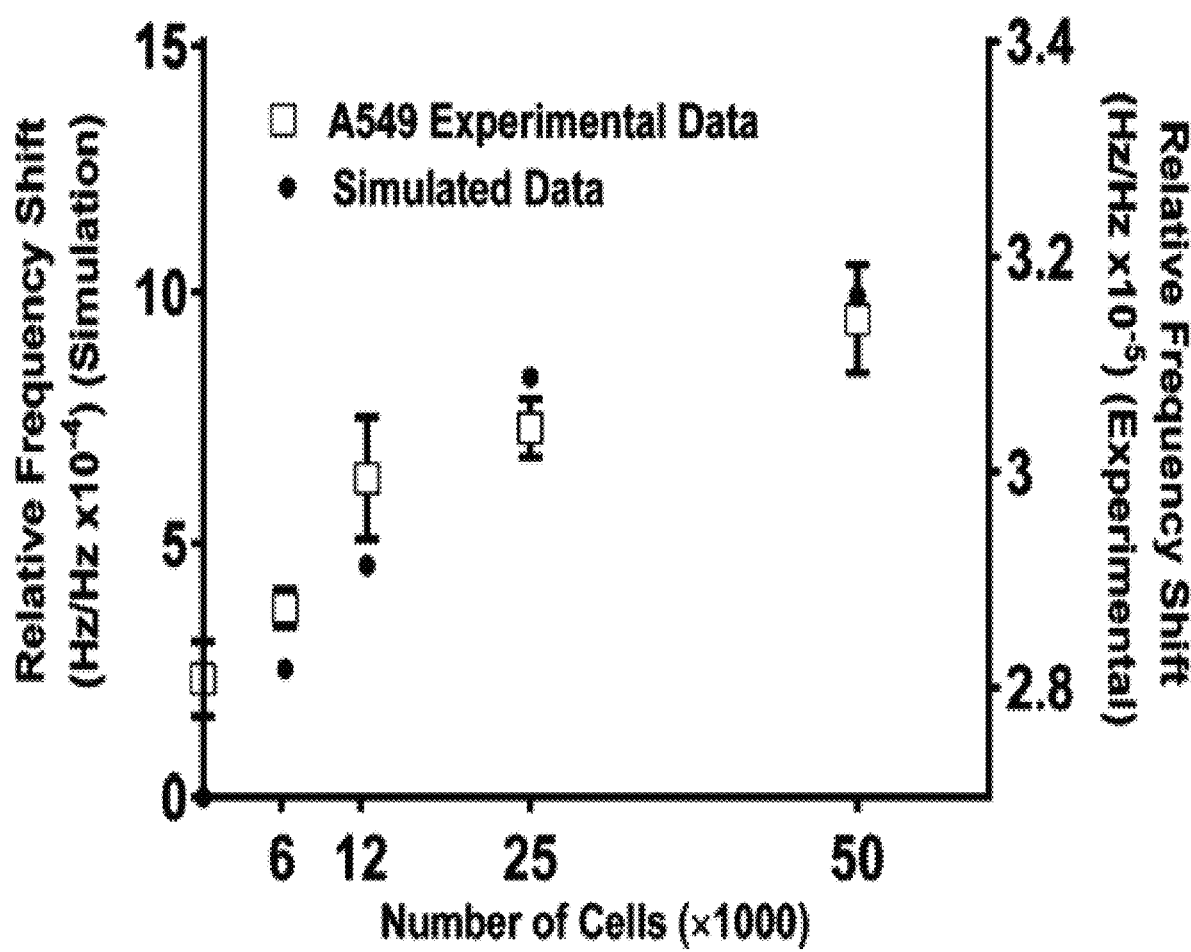
FIG. 6 shows that SAWs experiment data match the tendency of the simulation results on the ZnO coated sensor. Experimental data is plotted as mean±SEM. The data is a representative of a study that was performed in triplicates.

A working theoretical model based on the 3D COMSOL model was established by adding mass loading module that best mimicked the current bio-sensing device. This model allows for the tweaking of several parameters on the current device and running a simulation experiment without having to spend time and money on actual experiments. Towards this goal, the simulation studies were set up, wherein the weight of each individual cell was assumed to be 1 pg and different concentrations of cells were added to the ZnO surface (thickness 200 nm) on 36° Y-cut $LiTaO_3$ substrate by modifying the mass loading in the developed model. The cell concentrations simulated were 0, 6.25-, 12.5-, 25-, 50-, and 100- (×1,000) cells/microwell. After the cell (mass) loading was applied, the relative frequency response to the different cell concentrations was simulated (see FIGS. 2A-B). In order to normalize the frequency shift obtained in response to the cell concentration chance, relative frequency response, which is the frequency shift over the operation frequency ($\Delta f/f$), was the plotted. With the cell concentration increasing (hence the mass), the phase velocity of the substrate decreased which resulted in decreasing frequency. The simulated relative frequency shift was found to be about one order of magnitude higher than the experimental results, without applying any to the simulation when presenting the results. The mismatch between the raw simulation data presented and the experimental data is expected which may be attributed to the following factors. First, the weight of the individual cell was assumed to be 1 pg in the simulations for referencing purposes, whereas in actual experimentation the weight of the cells can differ significantly depending on the cell type. Second, the cells with media were placed on the bottom of the well in the actual experiments performed. On the other hand, the mass loading on the entire sensor chip surface was simulated for the 3D COMSOL model. Nonetheless, there is very good concordance of the simulated and experimental data is the very close match in the trends obtained (FIG. 6).

SAW Measurements Aid in Monitoring Growth of A549 3D Spheroid Cultures

Use of 3D cell culture techniques in cancer research is rapidly expanding due to the limited ability of traditional 2D culture to accurately model in vivo cell behavior. To test whether the SAW device is able to measure the cell density of 3D spheroids, (also referred to as tumoroids) growing on a fiber matrix, A549 cells were cultured on the matrix. A549 cells were allowed to grow on the scaffold for eight days and the culture media was changed every two days (FIG. 7A). The 3D scaffold alone was first measured as control and corresponding reading was designated as Day 0. On Days 4, 6, and 8 scaffolds were removed from the plate and assayed on the SAW sensor. Data shown in FIG. 7B demonstrates that the sensor was able to detect the change in density resulting from cell proliferation over time in the 3D environment. There was a linear increase in frequency shifts observed in A549 tumoroids with time. This increase was similar to increases in tumoroid size and number reported previously for other cancer cell lines. (Girard, Y. K. et al. *PLoS One* 8, (2013))

Based on the results, the acoustic measurement procedure seems to have no ill effect on cell viability in either the A549 cancer cell line or the RAW 264.7 macrophages. Cell proliferation was also unaffected by SAW measurements in A549. The device's ability to detect changes in cell density on the 3D scaffold over time along with its biocompatibility allows the device to be incorporated into 3D in vitro cancer models. The resulting platform enables continuous real-time measurement of cell growth in a 3D environment during bio assays including drug screens, multi-cell co-cultures, and gene knockdown/knockout etc.

Establishment of Tumoroid Co-Cultures to Identify Clinical Markers of Efficacy.

The inventors established conditions to co-culture tumor cells with ECs and CAFs to allow formation of robust MCTs. The human breast cancer cell lines, MCF7, BT474 and lung cancer cell line H1975 formed SCTs and MCTs (FIG. 9A) and MCTs showed slightly increased growth potential and high VEGF expression compared to SCTs. The presence of CAFs and ECs in the MCTs was confirmed by immunohistochemistry using anti-smooth muscle actin (SMA) and antivon Willebrand factor (vWF) antibodies for CAFs and ECs, respectively, followed by confocal microscopy (FIG. 9B). On day 5 after co-culture, CAFs were found dispersed throughout the MCT, whereas ECs were found mostly on the edge of the MCT.

Figure 9D:
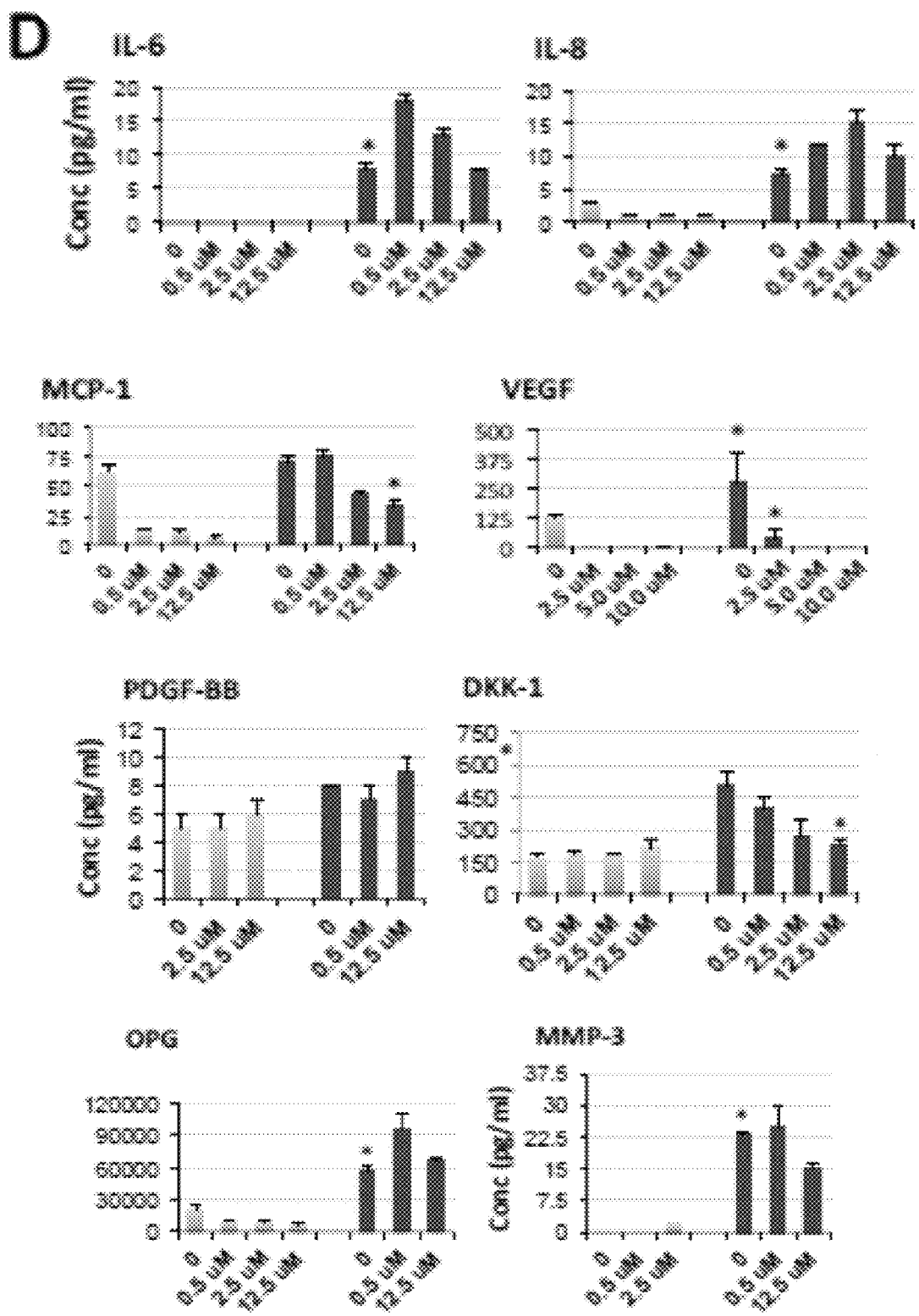
FIG. 9D is an image depicting growth of BT474 derived SCTs. (D) Determining IL-6 as a marker of clinical efficacy in lapatinib-treated tumoroids using Quantibody Array (Ray Biotech). BT474 tumoroids (SCTs, blue bars and MCTs, red bars) were cultured as in C, and the levels of factors in the day 5 culture supernatants were determined by ELISA. * p<0.05.

The inventors examined sensitivity of BT474-SCTs and -MCTs to lapatinib. BT474-SCTs cells are sensitive to lapatinib when cultured on PNS (IC50<2.5 µM), but in the presence of ECs and CAFs, BT474-MCTs showed significantly higher resistance to lapatinib (IC50>10 µM) (FIG. 9C). The results of a comparative analysis of culture supernatants of BT474-MCTs vs SCTs BT494 tumoroids led to identification of 7 biomarkers (FIG. 9D) that are specifically enhanced/altered in MCTs. These include, IL-6, IL-8, vascular endothelial growth factor (VEGF), monocyte chemotactic protein 1 (MCP-1), platelet derived growth factor BB (PDGF-BB), dickkopf-1 (DKK-1, inhibitor of Wnt signaling pathway), osteoprotegerin (OPG, a negative regulator of bone remodeling) and MMP-3, which have been implicated in tumor metastasis, angiogenesis, cancer stem cell amplification or drug resistance. In addition, five tumoroid biomarkers that are found expressed abundantly in MCTs (vs SCTs) and can be considered as predictors of clinical efficacy for lapatinib, included, a) marker for cell proliferation: Ki67, and b) stromal derived factors: IL-6, MCP-1, VEGF and DKK-1 (FIG. 9D).

Identification of these biomarkers in MCTs, which closely resemble the in vivo breast TME, makes the model as one that truly reflects in vivo TME. The inventors believe that these biomarkers implicated in breast TME have yet to be described in other 3D breast cancer tumor models. Together, these results show that PNS provides an excellent platform to produce robust SCTs and MCTs from tumor cell lines, in the absence or presence of stromal cells, which can be used to screen anti-cancer compounds.

Acoustic Biosensors for detection of cancer biomarkers.

Figure 10A:
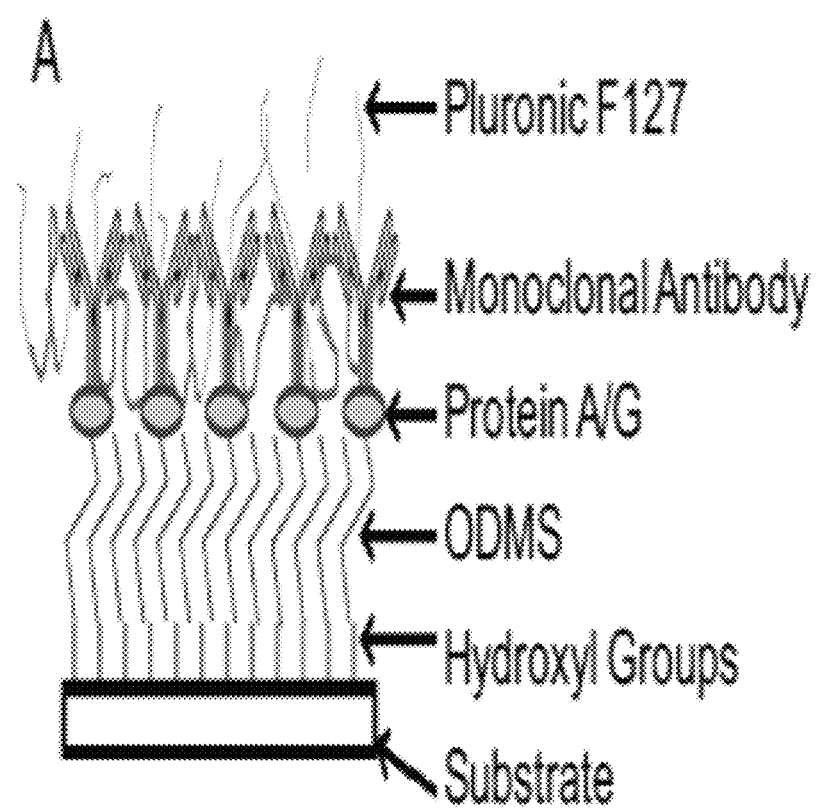
FIG. 10A is an image depicting the SAW device with an acoustic chip quantifying IL-6 concentration in tumoroid supernatants: A) Illustration of surface functionalization and steps involved.
Figure 10B:
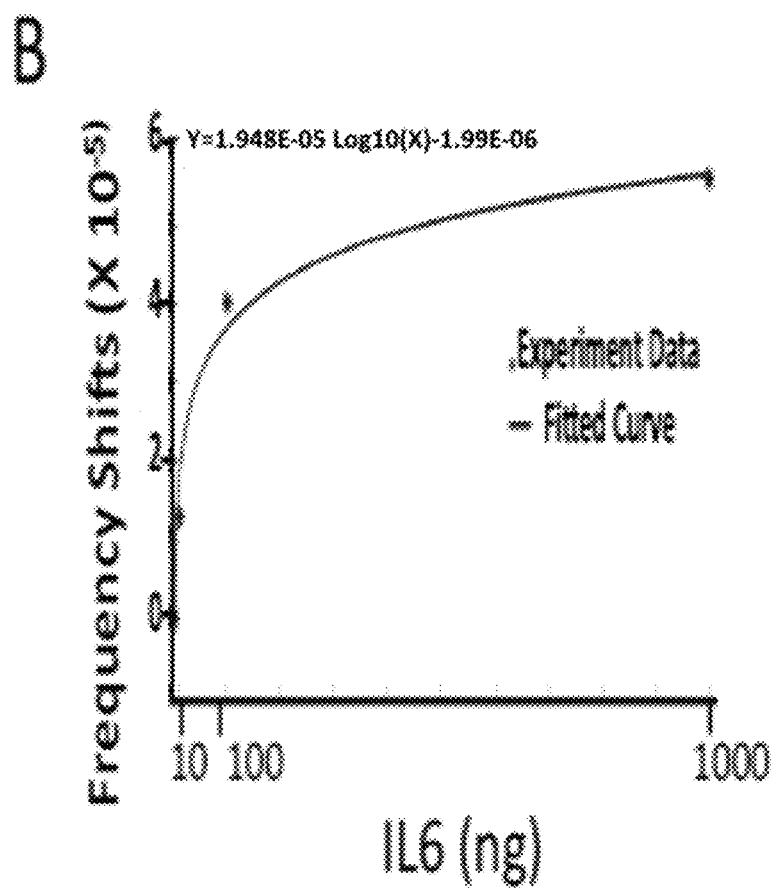
FIG. 10B is an image depicting the SAW device with an acoustic chip quantifying IL-6 concentration in tumoroid supernatants. (B) A standard curve was generated using human recombinant IL-6 using the surface acoustic wave (SAW) methodology.
Figure 10C:
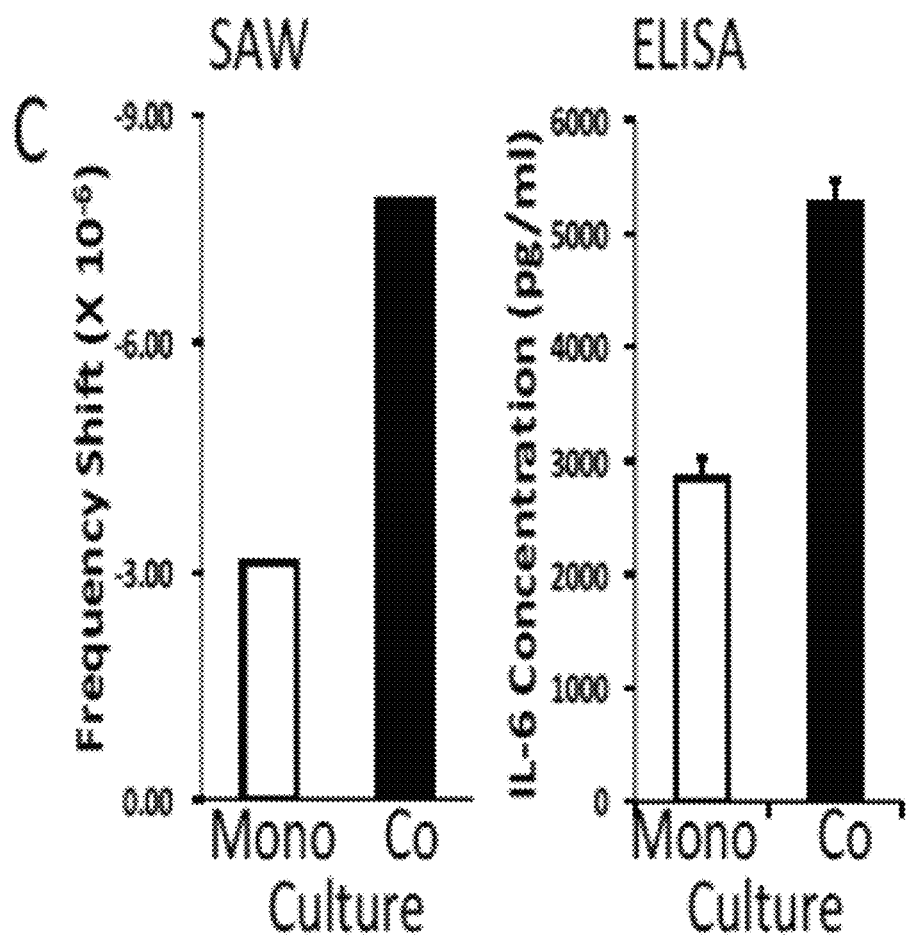
FIG. 10C is an image depicting the SAW device with an acoustic chip quantifying IL-6 concentration in tumoroid supernatants. Supernatants from single cell tumoroids (H460 cells) or multi-cell tumoroids (H460 co-culture) were collected on day 5 of culture and tested for the presence of human IL-6 either by the SAW methodology (left) or by standard ELISA (right) performed according the manufacturer's instructions (RayBiotech Inc.)
Figure 10D:
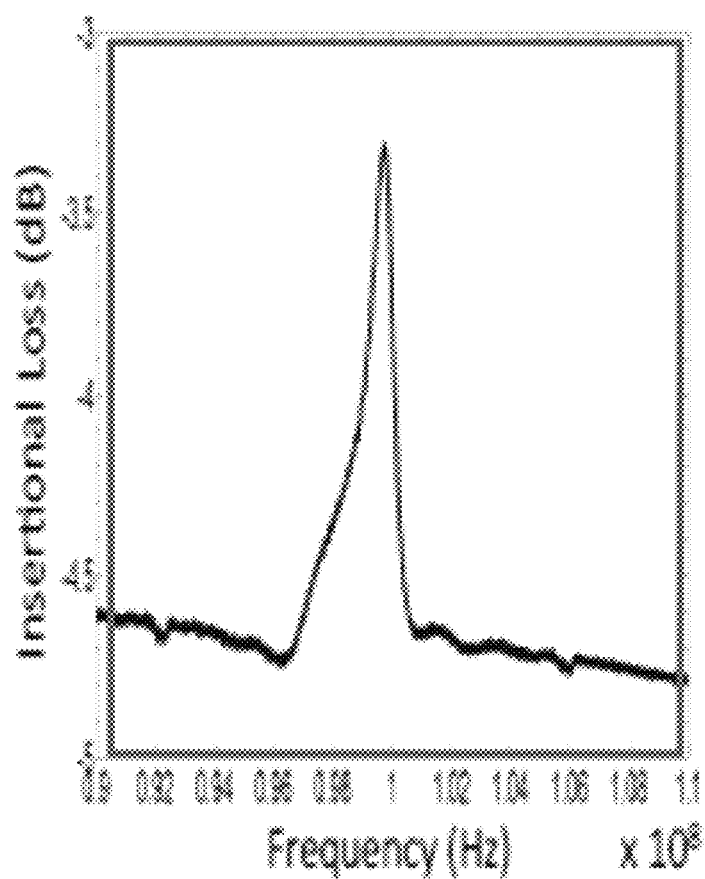
FIG. 10D is an image depicting the SAW device with an acoustic chip quantifying IL-6 concentration in tumoroid supernatants. (D) Experimentally measured insertion loss for 100 MHz transducers.

Since IL6 is a major tumor marker of clinical efficacy, the inventors investigated measuring IL6 with the developed SAW biosensing. Thus, the transducer surface was surface functionalized with monoclonal anti bodies, octadecyldimethylchlorosilane (ODMS), protein A/G and Pluronic F127 to minimize non-specific adsorption (FIG. 10A). A custom resonator circuit was employed to capture resonance frequency shift. The shift in frequency increased linearly with increasing IL-6 concentration ($R^2$=0.959) (FIG. 10B) and was found to be as sensitive as ELISA (FIG. 10C), however this measurement was obtained in real-time, within minutes. Also, we have recently fabricated and characterized a 100 MHz surface acoustic wave transducer (FIG. 10D) with an insertion loss as small as 3-4 dB, which will further improve the biomarker detection sensitivity.

Incorporating Microfluidic Based Perfusion to Tumoroid Culture to SAW Biosensing The system consists of a syringe pump (to precisely manipulate liquid in the microfluidic channels), two RF amplifiers (to optimize the oscillator circuit loop gain), a digital frequency counter (to quantify the frequency shift), a custom-designed passive filter (to optimize the oscillator circuit loop phase) and an oscilloscope (to visualize the frequency shift and oscillation real-time). The fabricated interdigitated transducer pairs are used as the feedback element of the amplifiers (FIG. 11). To measure prototype biomarkers such as VEGF, IL-6, IL-8, MMP3, TGF-β, each interdigitated electrode is coated with a corresponding antibody to each biomarker. Specifically, as the putative biomarkers are released into the media, they are captured by their corresponding antibody, which in turn leads to increase in its density. As the surface density increases by biomarker-antibody interaction, SAW velocity decreases, resulting in a reduction in the oscillation frequency that can be measured by the frequency counter. A representative fully integrated acoustic microfluidic chip designed, fabricated, experimentally characterized in the inventor's lab is shown in FIG. 12. FIG. 12 illustrates (a) a close-up of the interdigitated transducers; (b) the microfluidic channel mold before bonding; and (c) the completed, fully-integrated acoustic based microfluidic chip.

Currently, tumoroids are cultured in 96 well plates for 6 days with media changes on days 2 and 4. To imitate this in the microfluidic system, a 4-well chamber with 6.35 mm diameter (i.e. equivalent of a well in 96-well plate) (FIG. 11) is used which allows sampling data from 4 replicates at a time. Initially, the perfusion conditions are established with an appropriate flow rate (low vs high) to mimic media changes on days 2 and 4. Then, the tumoroid formation on days 6 and 10 in static (as control) vs. perfusion culture is compared. The microfluidic chamber is then disassembled and tumoroids are characterized for diameter by calcein AM staining and cell viability by CellTiter-Glo assay. Culture supernatants from static vs. perfused culture are compared for the expression of key biomarkers of clinical efficacy in static MCT culture such as VEGF, IL-6, TGF-β, MCP1 and MMP3.

Real-Time Sensing of Biomarkers in SCTs, MCTs and BdTs

To examine non-invasive monitoring of tumoroid growth and the concomitant changes in physiologic and metabolic events and changes, several tumor-specific biomarker expression are examined. For this purpose, either tumor cells (SCTs), mixtures of tumor and stromal cells (MCTs) or biopsy-derived tumoroids (BdTs) are deposited on the PNS and readings taken every 6 hours. For acoustical measurements to quantify glucose, lactate and tumor biomarker concentrations, the interdigitated transducers patterned on the substrate are connected to a custom-designed oscillatory circuit to increase measurement sensitivity as compared to commonly used measurement methods such as a vector voltmeter.

Experimental Methods
Experimental Protocol for SAW Measurement:

A549 human lung adenocarcinoma cells were maintained in RPMI media containing 10% fetal bovine serum (FBS) and 1% penicillin streptomycin. RAW-264.7 murine macrophages (used as an example of a non-cancerous cell) were maintained in Dulbecco's modified eagle medium (DMEM) media containing 10% FBS and 1% penicillin streptomycin. All cells were cultured in a humidified incubator at 37° C. in a 5% CO2 atmosphere. Cells were collected via trypsinization and counted using a hemocytometer. For SAW measurement of cells in suspension, cell suspensions of decreasing concentration were prepared by serial dilution in phosphate buffered saline (PBS) containing 1% FBS. Half a minute after the frequency counter started to record, 100 µL of each suspension was placed on the chip of test group to record the relative frequency response for a duration of 10 minutes. After recording each sample, the cell suspension was removed by vacuum and the well was washed with three changes of PBS followed by three changes of water to clean the sensing area.

Figure 8:
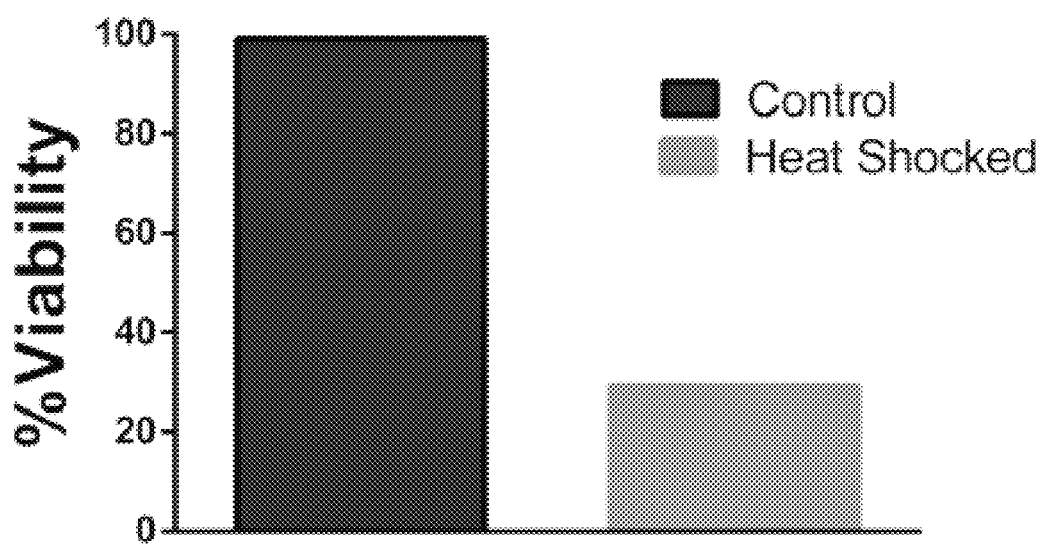
FIG. 8 is an image depicting quantification of Cell Growth in 2D Cultures. A549 cells where either left untreated (Control) or subjected to heat (Heat Shocked) at 56° C. for 15 min. At the end of the heat shock the cells were mixed with trypan blue solution and processed for cell counting using the T20TM automated cell counter according to the manufacturer's instructions (Bio-Rad). The data was plotted as % viability wherein the viability of the control cells was set at 100%.

Experimental Protocol for Measuring Cell Viability:

The cell viability was determined using trypan blue staining in combination with a T20™ automated cell counter (Bio-Rad). Cell suspension was mixed with trypan blue at a ratio of 1:2 respectively and the resulting cell suspension was loaded on to a cassette for measurement in the cell counter. The T20™ uses microscopy in conjunction with an algorithm to calculate the total cell count and assesses the cell viability by trypan blue exclusion without any interference from the user. The advantage of this methodology is that it ensures reproducibility in the cell count independent of the users. Additionally, the instrument was validated for measuring the cell viability by using a cell suspension sample that was heated for 15 min at 56° C. to induce cell death and show that the cell counter was able to detect increase in cell death by counting the number of trypan blue positive dead cells. (FIG. 8).

Experimental Protocol for Measuring Cell Proliferation:

To examine any long term effects on cell proliferation a re-plating experiment was performed in which cells were collected and then seeded onto a 96 well culture plate after SAW measurements and allowed to grow for three days. Cell number and morphology were compared to untested control cells by both light microscopy (Olympus BX51) and by staining the cells with Hoechst 33342 (NucBlue, Life Technologies) and then capturing images using fluorescence microscopy (Olympus BX51). This assay was designed to reveal any changes to the cell proliferation rate as a result of SAW measurement.

Experimental Protocol for Culturing 3D Tumoroids:

For growing cell cultures in 3-dimension (3D), a unique fibrous scaffold (3P scaffold) that promotes the growth of 3D "tumoroids" when seeded with cancer cells was used. 3P scaffold was prepared by electrospinning as described in Girard (2013), herein incorporated by reference into this disclosure. (Girard, Y. K. et al. *PLoS One* 8, (2013))

Briefly, an mPEG-PLA block copolymer was prepared by ring-opening polymerization. Briefly, 3,6-dimethyl-1, 4-dioxane-2, 5-dione (LA) (Fisher) was dried in a vacuum oven at 40 uC overnight. 1 g of mono-methoxy poly(ethylene glycol) (mPEG) was flame dried in a 100 ml three-necked round-bottom flask and stirred at 80 uC for 2 hours under vacuum. 4 g of dried LA polymer and 0.2 wt % stannous octoate (Sn(Oct)2) were added to the flask under the protection of argon gas. The mixture was dissolved in 20 ml anhydrous toluene and heated at 140 uC under argon gas for 5 hours. Solid products of the diblock copolymers were obtained by adding the polymer solution to ice cold diethyl ether. The product were dissolved in dichloromethane and precipitated in cold diethyl ether twice, for purification. The final copolymer was dried in a vacuum oven at 50 uC for 48 hours. The prepared polymer was characterized by FTIR using a Nexus spectrometer and 1HNMR using a Bruker 250 spectrometer. (Girard 2013).

A 3P scaffold was constructed by dissolving 1 g of poly(lactic co-glycolic acid) and 3 g of mPEG-PLA polymer in a solution of dichloromethane and chloroform (80/20 v/v). For the construction of the PLGA scaffold a 3% (w/v) of PLGA in a solution of dichloromethane and chloroform (80/20 v/v) was used. The solutions were electrospun at a positive voltage of 20 kVDC and a flow rate of 0.2-0.5 ml/hr using a high voltage power supply (Gamma High Voltage Research, USA) and a syringe pump (kD Scientific). The fibers were collected on an aluminum covered copper plate at a fixed distance of 20 cm. The scaffolds were cut to approximately 767 mm$^2$ and placed in 96 well plates, sterilized in isopropyl alcohol, washed three times in PBS then additionally sterilized by exposure to high intensity UV light for one hour. (Girard 2013).

Scaffold was placed into a 96 well plate and 5,000 A549 cells were seeded into each well in RPMI media. Cells were allowed to grow on the scaffold for eight days and the culture media was changed every two days. The tumoroids along with the scaffold were used for SAW measurement with scaffold alone being used as a comparative control. Successful growth of cells in 3D was confirmed by staining the cells with Hoechst 33342 (NucBlue, Life Technologies) and then capturing images using fluorescence microscopy (Olympus BX51).

CONCLUSION

There are several translational implications for the device. Acoustic biosensing involves a highly sensitive and tunable SAW (37-46), which can be performed without any electrode touching the tumoroids and acoustical response can be acquired independent of existence of a magnetic/electrical field and iron oxide/MnO nanoparticles in the flow field. The potential for miniaturization and integration of complex functions into "multi-cell tumoroids on chip" exists, which revolutionizes real-time tracking of biomarkers and clinical diagnostics and prognostics of cancers in a point-of-care setting for personalizing therapy. Also, monitoring of physiologic/metabolic tumor markers via acoustic biosensing increases resemblance of tumoroid cultures to in vivo tumors and provides a precise, stable, and well-defined culture environment for cellular assays.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A shear horizontal-surface acoustic wave device for detecting and quantifying cell growth and viability comprising:
    two pairs of resonators formed on a lithium tantalate substrate wherein each resonator is comprised of at least two interdigital transducers, each having at least one pair of reflecting fingers;
    at least one pH measurement electrode, at least one oxygen measurement electrode, at least one impedance measurement electrode and at least one interdigitated electrode formed on the lithium tantalate substrate;
    an oscillatory circuit system connected to the two pairs of resonators, the oscillatory circuit system comprising
        a pair of band pass filters, each filter connected to one end of each pair of resonators;
        a pair of amplifiers, each amplifier connected to an opposing end of each pair of resonators wherein the connection of each band pass filter and each amplifier to each pair of resonators forms a closed-loop system;
        an oscilloscope connected to the closed loop system by a T-connector; and
        a digital frequency counter connected to the closed loop system by the T-connector; and
    at least one Y-shaped polydimethylsiloxane (PDMS) microfluidic channel bonded to the lithium tantalate substrate wherein the at least one microfluidic channel contains an inlet access opening, an outlet access opening, at least one carbon dioxide access opening and a resealable access opening to a chamber;
    wherein each transducer is coated with a substance selected from the group consisting of zinc oxide (ZnO), silicon oxide (SiO$_2$), silicon nitride (Si3N4), titanium oxide (TiO2), poly(methyl methacrylate) (PMMA), poly(chloro-p-xylylene) (Parylene-C) and an epoxy-based negative photoresist.

2. The device of claim 1, wherein the lithium tantalite substrate is a 36° Y-cut LiTaO$_3$ substrate.

3. The device of claim 1, wherein number of reflecting fingers is 30 pairs.

4. The device of claim 1, wherein wavelength of the reflecting fingers is about 297 µm.

5. The device of claim 1, wherein height of the reflecting fingers is about 100 nm.

6. The device of claim 1, wherein width of the reflecting fingers is about 74.25 µm.

7. The device of claim 1, wherein the coating on each transducer is ZnO.

8. The device of claim 7, wherein thickness of the ZnO is about 200 nm.

9. The device of claim 1, wherein a velocity of a surface acoustic wave in the device is about 4160 m/s.

10. The device of claim 1, wherein operation frequency of the device is about 14.05 MHz.

11. A system for detecting and quantifying cell growth comprising:
    a shear horizontal-surface acoustic wave (SH-SAW) biosensor comprising:
        two pairs of resonators formed on a lithium tantalate substrate wherein each resonator is comprised of at least two interdigital transducers, each having at least one pair of reflecting fingers;
        at least one pH measurement electrode, at least one oxygen measurement electrode, at least one impedance measurement electrode and at least one interdigitated electrode formed on the lithium tantalate substrate;

an oscillatory circuit system connected to the two pairs of resonators, the oscillatory circuit system comprising
- a pair of band pass filters, each filter connected to one end of each pair of resonators;
- a pair of amplifiers, each amplifier connected to an opposing end of each pair of resonators wherein the connection of each band pass filter and each amplifier to each pair of resonators forms a closed-loop system;
- an oscilloscope connected to the closed loop system by a T-connector; and
- a digital frequency counter connected to the closed loop system by the T-connector; and at least one Y-shaped polydimethylsiloxane (PDMS) microfluidic channel bonded to the lithium tantalate substrate wherein the at least one microfluidic channel contains an inlet access opening, an outlet access opening, at least one carbon dioxide access opening and a resealable access opening to a chamber;

a syringe pump to precisely manipulate liquid into microfluidic channels of the SH-SAW biosensor;

a signal generator connected to the SH-SAW biosensor wherein the signal generator generates a signal to the SH-SAW biosensor; and a computer processor to record data;

wherein each transducer is coated with a substance selected from the group consisting of zinc oxide (ZnO), silicon oxide ($SiO_2$), silicon nitride (Si3N4), titanium oxide (TiO2), poly(methyl methacrylate) (PMMA), poly(chloro-p-xylylene) (Parylene-C) and an epoxy-based negative photoresist.

12. The system of claim 11, wherein the lithium tantalite substrate is a 36° Y-cut $LiTaO_3$ substrate.

13. The system of claim 11, wherein the SH-SAW biosensor has 30 pairs of reflecting fingers.

14. The system of claim 11, wherein the coating on each transducer is ZnO.

* * * * *

UNITED STATES PATENT AND TRADEMARK OFFICE
CERTIFICATE OF CORRECTION

PATENT NO. : 11,016,062 B2
APPLICATION NO. : 16/722210
DATED : May 25, 2021
INVENTOR(S) : Shyam S. Mohapatra et al.

It is certified that error appears in the above-identified patent and that said Letters Patent is hereby corrected as shown below:

In the Specification

Please amend Column 1, Lines 25-30 as follows:
STATEMENT OF GOVERNMENT INTEREST
This invention was made with government support under R01 CA152005 awarded by the National Institutes of Health. The government has certain rights in the invention.

Signed and Sealed this
Thirtieth Day of May, 2023

Katherine Kelly Vidal
*Director of the United States Patent and Trademark Office*